United States Patent
Prechtl et al.

(10) Patent No.: US 6,569,355 B1
(45) Date of Patent: May 27, 2003

(54) CHIRAL COMPOUNDS, AND THEIR USE AS CHIRAL DOPANTS FOR THE PREPARATION OF CHOLESTERIC LIQUID-CRYSTALLINE COMPOSITIONS

(75) Inventors: Frank Prechtl, Frankfurt (DE); Sylke Haremza, Neckargemünd (DE); Frank Meyer, Heidelberg (DE); Robert Parker, Mannheim (DE); Volkmar Vill, Hamburg (DE); Gunnar Gesekus, Hamburg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 300 days.

(21) Appl. No.: 09/677,861

(22) Filed: Oct. 3, 2000

(30) Foreign Application Priority Data

Oct. 12, 1999 (DE) ......................... 199 49 284

(51) Int. Cl.[7] ............... C09K 19/52; A61K 7/42
(52) U.S. Cl. ............ 252/299.01; 424/59; 252/582
(58) Field of Search ............ 252/299.01, 582, 252/588; 424/78.03, 401, 59–60, 47

(56) References Cited

U.S. PATENT DOCUMENTS

| | | | |
|---|---|---|---|
| 5,744,057 A | 4/1998 | Meyer et al. | 252/299 |
| 5,753,141 A | * 5/1998 | Siemensmeyer et al. | 252/299.62 |
| 5,780,629 A | 7/1998 | Etzbach et al. | 544/296 |
| 5,788,880 A | 8/1998 | Schierlinger et al. | 252/299 |
| 5,827,449 A | 10/1998 | Hanelt et al. | 252/299 |
| 5,833,880 A | 11/1998 | Siemensmeyer et al. | 252/299 |
| 5,851,277 A | 12/1998 | Müller-Rees et al. | 106/287 |
| 6,099,751 A | 8/2000 | Meyer et al. | 252/299 |
| 6,136,225 A | 10/2000 | Meyer et al. | 252/299 |
| 6,136,251 A | 10/2000 | Etzbach et al. | 264/297 |

FOREIGN PATENT DOCUMENTS

| | | |
|---|---|---|
| DE | 43 42 280 | 6/1995 |
| DE | 44 08 171 | 9/1995 |
| DE | 195 32 408 | 3/1997 |
| DE | 195 41 820 | 5/1997 |
| DE | 196 11 101 | 9/1997 |
| DE | 196 19 460 | 11/1997 |
| DE | 196 38 797 | 3/1998 |
| DE | 197 38 368 | 3/1999 |
| DE | 197 38 369 | 3/1999 |
| EP | 750 029 | 12/1996 |
| GB | 2 314 839 | 1/1998 |
| WO | WO 95/16007 | 6/1995 |

OTHER PUBLICATIONS

C.G. Roffey "Photopolymerizable film–forming materials" Phtopolymerization of Surface Coatings (1982) pp. 137–208.

Spohr et al. "Inhibitors of endo-(α-mannosidase. Part I[1] Derivatives of 3–O–(α–D–glucopyranosyl)–D–mannopyranose" Canadian Journal of Chemistry, vol. 71, No. 11, (1993) pp. 1919–1927.

Finkelmann et al. "Synthesis of Cholestric Liquid Crystalline Polymers, Polyreactions in Ordered Systems" Markromol. Chem. vol. 179 (1978) pp. 829–832.

Kinashi et al. "Syntheses and Mesomorphic Properties of New Liquid Crystalline Materials Involving Piperazine Skeleton" Mol. Cryst. Liq, Cryst. vol. 67 (1981) pp.49–58.

Dahloff "Synthesis of Mesogenic 4– and 6–O–Alkyl D–glucitols" Liebigs Ann. Chem. (1991) pp. 463–467.

Dahloff "Mesogenic 4–O–alkyl–D–Flucoses via Methyl 4,6–O–Alkylidene–D–glucopyranosides" Liebigs Ann. Chem. (1993) pp. 1063–1067.

Ho et al. "Chiral Liquid Crystalline Compounds from D–(+)–Glucose" Tetrhedron vol. 51 (1995) pp. 7373–7388.

Smits et al. "Non–amphillic Carbohydrate Liquid Crystals Containing an Intact Monosacchride Moiety" Mol. Cryst. Liq. Cryst. vol. 260 (1995) pp. 185–199.

Smits et al. "Cholesteric Carbohydrate Liquid Crystals Incorporating an Intact Glucopyranose Moiety" Mol. Cryst. Liq. Cryst. vol. 299(1997) pp. 427–432.

Miethchen et al. "Amphiphile Fluorglucose–und Fluorseyllitol–Derivate" Chem. Ber. vol. 126 (1993) pp. 1707–1712 Abstract (English).

Vill et al. "Molekulares Vuerdrillungsvermögen veo Kilhenhydrat–Derivaten" Z. Naturforsch vol. 43a (1988) pp. 1119–1125 Abstract (English).

* cited by examiner

Primary Examiner—Mark F. Huff
Assistant Examiner—Jennifer R. Sadula
(74) Attorney, Agent, or Firm—Keil & Weinkauf

(57) ABSTRACT

The use of compounds of the general formula I

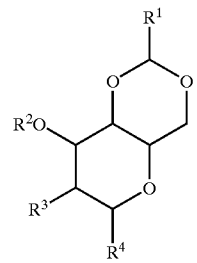

in which the substituents are as defined in the description, as chiral dopants for nematic or cholesteric liquid crystals for the generation of layers which reflect in color in the UV or IR region or for the preparation of pigments having a liquid-crystalline cholesteric order.

14 Claims, No Drawings

CHIRAL COMPOUNDS, AND THEIR USE AS CHIRAL DOPANTS FOR THE PREPARATION OF CHOLESTERIC LIQUID-CRYSTALLINE COMPOSITIONS

The present invention relates to chiral compounds and to their use as chiral dopants for nematic or cholesteric liquid crystals for the generation of layers which reflect in color in the UV or IR region or for the preparation of pigments having a liquid-crystalline, cholesteric order.

Cholesteric liquid crystals (CLCs) reflect circular-polarized electromagnetic radiation in a wavelength region which is dependent on the helical structure of the CLC. The central wavelength of the reflection band is determined by the pitch p of the helical structure, and the width of the band is determined by the optical anisotropy of the mesogens. The central wavelength of the reflection band, which is referred to below as the reflection wavelength, is dependent on the viewing angle. The direction of rotation of the reflected light corresponds to the direction of rotation of the cholesteric helix.

Cholesteric liquid-crystal mixtures generally comprise one or more optically active components for inducing a chiral structure. For example, cholesteric liquid-crystal mixtures can consist of a nematic base material and one or more optically active dopants, which generate either a right- or left-handed twist in the nematic phase which determines the direction of rotation of the reflected circular-polarized light.

Numerous compounds have been disclosed as chiral dopants for liquid-crystalline phases (for example in DE-A 43 42 280, DE-A 195 41 820 and DE-A 196 11 101, and in GB-A-2 314 839 and WO 98/00428).

For left-handed helical materials, cholesterol compounds are frequently suitable; apart from chirality, these introduce sufficiently mesogenic properties in order to generate a stable mesophase. Such compounds are described, for example, by H. Finkelmann, H. Ringsdorf et al., in Makromol. Chem. 179, 829–832 (1978). However, these compounds have the disadvantage of complex synthesis and a high preparation price.

It is an object of the present invention to provide novel chiral compounds which are suitable for the preparation of cholesteric liquid-crystalline compositions and which do not have the abovementioned disadvantages.

We have found that this object is achieved in accordance with the invention by the use of compounds of the general formula I

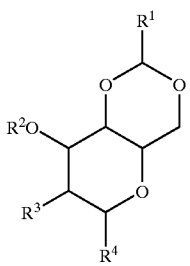

I in which the substituents, independently of one another, have the following meanings:

$R^1$ is $Z^1$—$Y^1$—$(A^1)_m$—$Y^2$—$M^1$—$Y^3$—$(A^2)_n$—$Y^4$—;
$R^2$ is hydrogen, $C_1$–$C_{12}$-alkyl, $C_1$–$C_{12}$-alkylcarbonyl, aryl, arylcarbonyl or $Z^2$—$Y^5$—$(A^3)_o$—$Y^6$—$M^2$—$Y^7$—$(A^4)_p$—$Y^{11}$—;
$R^3$ is hydrogen, $C_1$–$C_{12}$-alkyl, aryl or $OR^5$;
$R^4$ is hydrogen, $C_1$–$C_{12}$-alkyl, aryl or $OR^6$;
$R^5$ and $R^6$ are hydrogen, $C_1$–$C_{12}$-alkyl, $C_1$–$C_{12}$-alkylcarbonyl, aryl, arylcarbonyl or $Z^3$—$Y^8$—$(A^5)_q$—$Y^9$—$M^3$—$Y^{10}$—$(A^6)_r$—$Y^{12}$—;
$A^1$ to $A^6$ are spacers having a chain length of from 1 to 30 carbon atoms;
$M^1$ to $M^3$ are mesogenic groups;
$Y^1$ to $Y^{10}$ are chemical bonds, —O—, —S—, —C(=O)—, —C(=O)—O—, —O—C(=O)—, —CH=CH—C(=O)—O—, —O—C(=O)—O—, —C(=O)—N(R)— or —(R)N—C(=O)—, —CH$_2$—O—, —O—CH$_2$—, —CH=N—, —N=CH— or —N=N—;
$Y^{11}$ and $Y^{12}$ are chemical bonds, —C(=O)—, —O—C(=O)—, —CH=CH—C(=O)—, —(R)N—C(=O)—, —CH$_2$— or —O—CH$_2$—;
R is hydrogen or $C_1$–$C_4$-alkyl;
$Z^1$ to $Z^3$ are hydrogen, $C_1$–$C_{12}$-alkyl, polymerizable groups or radicals carrying polymerizable groups;
m to r is are 0 or 1,
where the radicals $A^1$ to $A^6$, $Y^1$ to $Y^{10}$, $Y^{11}$ and $Y^{12}$ and $Z^1$ to $Z^3$ may be identical or different, and where, in the case where one or more of the indices m to r are zero, at least one of the radicals Y in each case adjacent to A is a chemical bond,
as chiral dopants for nematic or cholesteric liquid crystals for the generation of layers which reflect in color in the UV or IR region or for the preparation of pigments having a liquid-crystalline, cholesteric order.

Examples of alkyl radicals which may be mentioned for $R^2$ to $R^6$ and for $Z^1$ to $Z^3$ are branched or unbranched $C_1$–$C_{12}$-alkyl chains, for example methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, 2-ethylhexyl, n-nonyl, n-decyl, n-undecyl and n-dodecyl.

Preferred alkyl radicals which may be mentioned for $R^2$ to $R^6$ from the abovementioned list are the branched or unbranched $C_1$–$C_6$-alkyl chains, for example methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 2-ethylpropyl and n-hexyl.

Preferred alkyl radicals which may be mentioned for $Z^1$ to $Z^3$ from the abovementioned list are the branched or unbranched $C_4$–$C_{10}$-alkyl chains, for example n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, n-heptyl, n-octyl, 2-ethylhexyl, n-nonyl and n-decyl.

The term "aryl" for $R^2$ to $R^6$ is taken to mean aromatic rings or ring systems having 6 to 18 carbon atoms in the ring system, for example phenyl or naphthyl, which can be unsubstituted or substituted by one or more radicals, such as halogen, for example fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals.

Alkyl and arylcarbonyl radicals which may be mentioned for $R^2$, $R^5$ and $R^6$ are carbonyl groups with the abovementioned $C_1$–$C_{12}$-alkyl chains or the abovementioned aromatic rings or ring systems having 6 to 18 carbon atoms.

Suitable spacers $A^1$ to $A^6$ are all groups known for this purpose. The spacers generally contain from 1 to 30, preferably from 1 to 12, particularly preferably from 1 to 6, carbon atoms and consist of predominantly linear aliphatic groups. They may be interrupted in the chain, for example by non-adjacent oxygen or sulfur atoms or imino or alkylimino groups, for example methylimino groups. Suitable substituents for the spacer chain are fluorine, chlorine, bromine, cyano, methyl and ethyl.

Examples of representative spacers are the following:

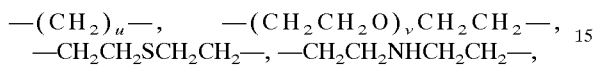

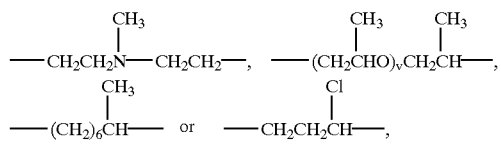

where u is from 1 to 12, and v is from 1 to 3.

Preferred spacers are ethylene, propylene, n-butylene, n-pentylene and n-hexylene.

It is furthermore also possible to link one or more of the mesogenic radicals $M^1$ to $M^3$ directly to the associated radicals $Z^1$ to $Z^3$ without spacers. In these cases, the indices m, o and q are 0, and $Y^1/Y^2$, $Y^5/Y^6$ and $Y^8/Y^9$ together are a chemical bond, in particular a single chemical bond.

The radicals $M^1$ to $M^3$ can be all known mesogenic groups.

Particularly suitable mesogenic groups are those of the formula $$(-T-Y^{17})_w-T-$$

in which the variables have the following meanings:

T are identical or different divalent, saturated or unsaturated, isocyclic or heterocyclic radicals, $Y^{17}$ are groups as defined for $Y^1$ to $Y^{10}$, and w is 0, 1, 2 or 3, where, in the case where w>0, both the radicals T and the groups $Y^{17}$ may in each case be identical to or different from one another.

w is preferably 1 or 2.

The radicals T may also be ring systems which are substituted by fluorine, chlorine, bromine, cyano, hydroxyl or nitro. Preferred radicals T are the following:

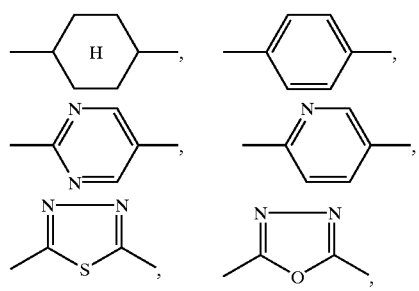

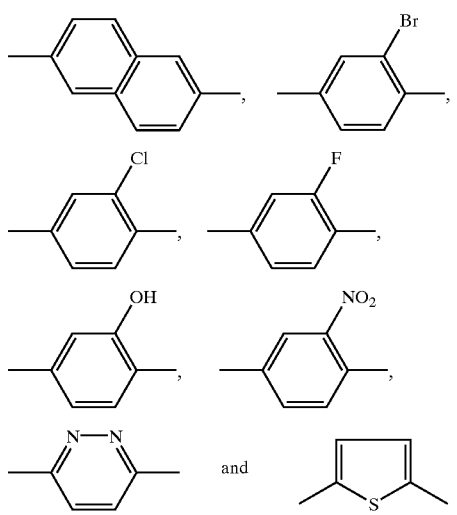

Examples of preferred mesogenic groups M are the following:

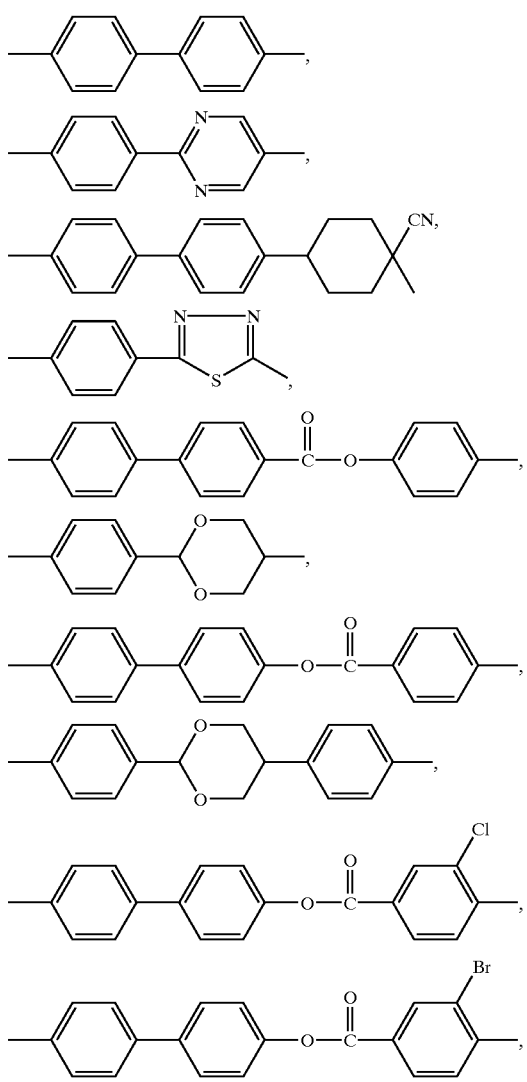

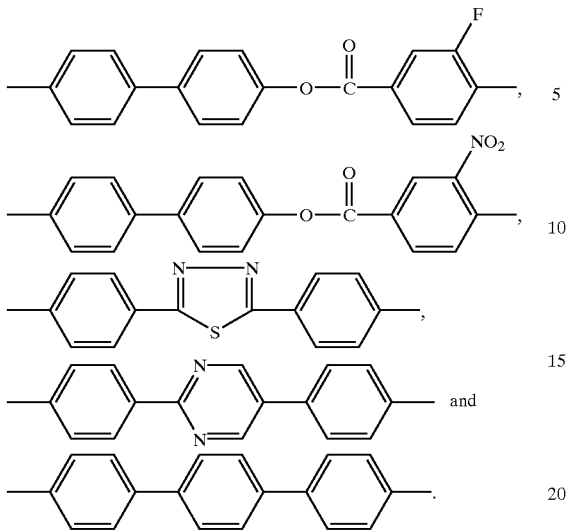

Particular preference is given to mesogenic groups M of the following formulae

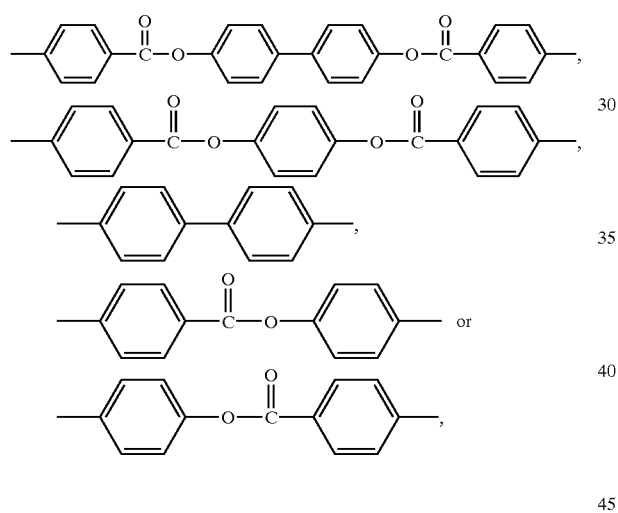

where each aromatic ring may carry up to three identical or different substituents from the following group:

hydrogen, $C_1$–$C_{20}$-alkyl, $C_1$–$C_{20}$-alkoxy, $C_1$–$C_{20}$-alkoxycarbonyl, $C_1$–$C_{20}$-monoalkylaminocarbonyl, $C_1$–$C_{20}$-alkylcarbonyl, $C_1$–$C_{20}$-alkylcarbonyloxy, $C_1$–$C_{20}$-alkylcarbonylamino, formyl, halogen, cyano, hydroxyl and nitro.

Besides hydrogen, fluorine, chlorine, bromine, cyano, formyl and hydroxyl, preferred substituents for the aromatic rings are, in particular, short-chain aliphatic radicals, such as methyl, ethyl, n-propyl, i-propyl, n-butyl, i-butyl, sec-butyl, tert-butyl and alkoxy, alkoxycarbonyl, alkylcarbonyl, alkylcarbonyloxy, alkylcarbonylamino and monoalkylaminocarbonyl radicals which contain these alkyl groups.

The outer benzene rings of the particularly preferred groups M preferably have the following substitution patterns:

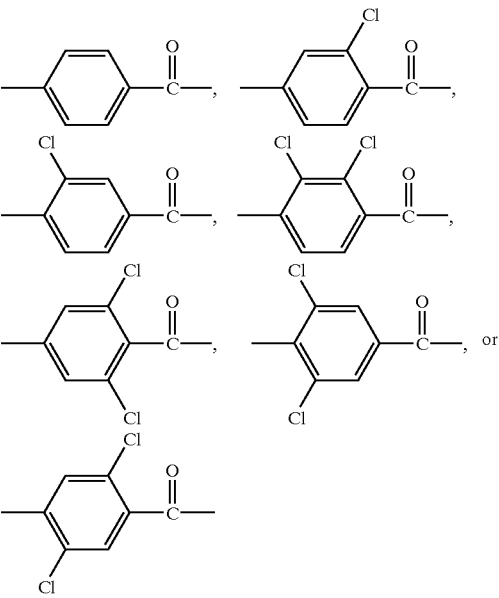

or they are substituted analogously by F, Br, $CH_3$, $OCH_3$, CHO, $COCH_3$, $OCOCH_3$ or CN instead of Cl, where the substituents may also be mixed. Mention may furthermore be made of the structures

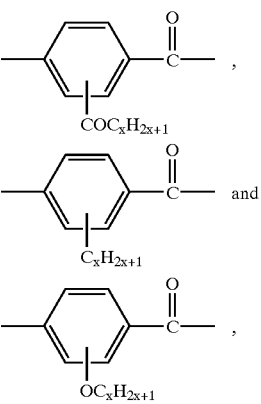

in which x is from 2 to 20, preferably from 8 to 15.

The preferred substitution patterns of the central benzene ring of the particularly preferred groups M are

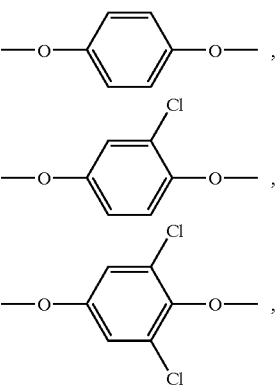

-continued
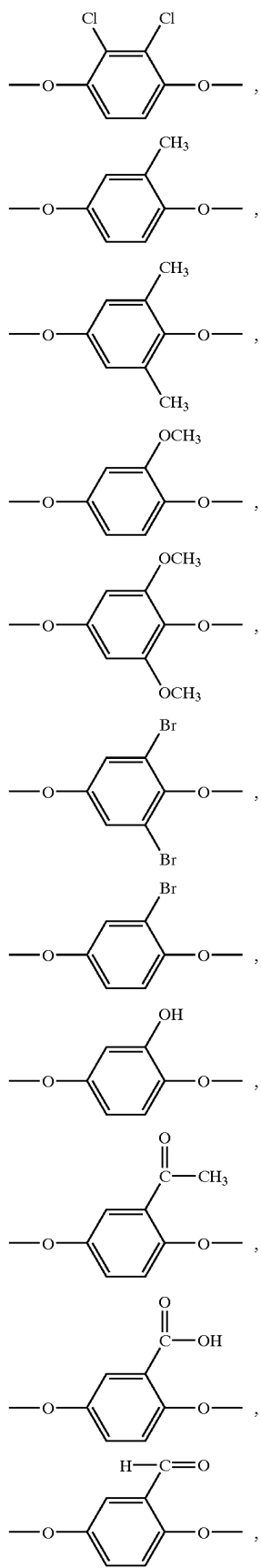
-continued
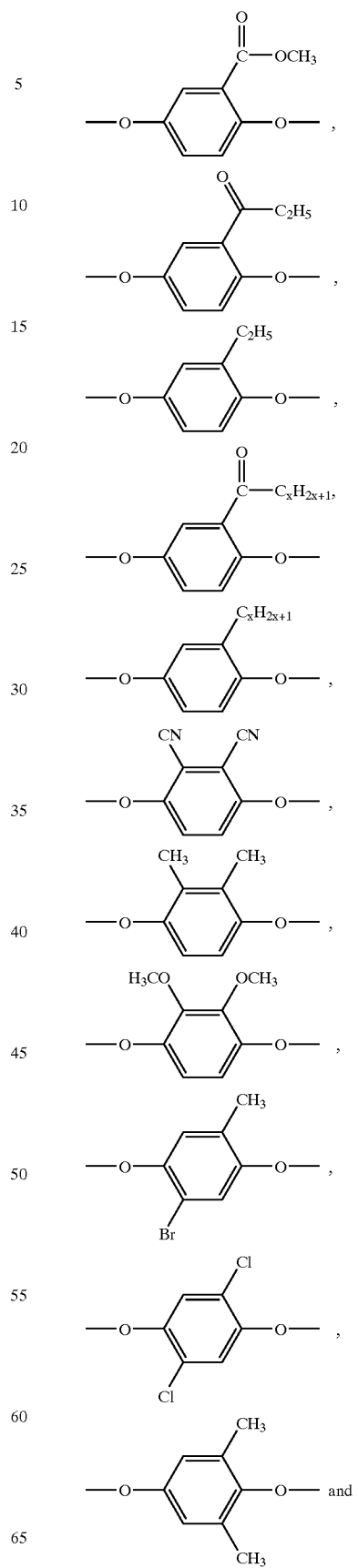

-continued

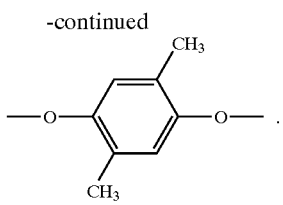

Alkyl radicals which may be mentioned for R and for branched or unbranched $C_1C_4$-alkyl chains are preferably methyl, ethyl, n-propyl, 1-methylethyl, n-butyl, 1-methylpropyl, 2-methylpropyl and 1,1-dimethylethyl.

Preferred radicals for $Z^1$ to $Z^3$ are the following:

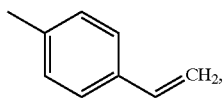

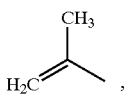

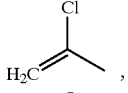

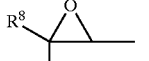

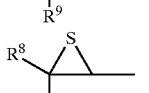

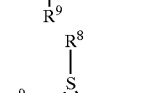

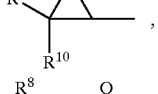

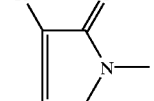

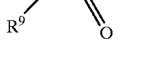

—N=C=O, —N=C=S, —O—C≡N, —COOH, —OH and $NH_2$ where the radicals $R^8$ to $R^{10}$ may be identical or different and are hydrogen or $C_1$–$C_4$-alkyl, such as methyl, ethyl, n-propyl, isopropyl, n-butyl, isobutyl, sec-butyl or tert-butyl. Of the reactive polymerizable groups, the cyanates can spontaneously trimerize to cyanurates and are therefore preferred. The other groups mentioned require further compounds containing complementary reactive groups for polymerization. Thus, for example, isocyanates can polymerize with alcohols to give urethanes and with amines to give urea derivatives. An analogous situation applies to thiiranes and aziridines. Carboxyl groups can be condensed to give polyesters and polyamides. The maleimido group is particularly suitable for free-radical copolymerization with olefinic compounds, such as styrene. The complementary reactive groups here can either be present in a second compound according to the invention which is mixed with the first or they can be incorporated into the polymeric network by means of auxiliary compounds containing 2 or more of these complementary groups.

Polymerizable groups which may be mentioned in particular are acrylate and methacrylate.

Particular preference is given to the chiral dopants of the general formula Ia,

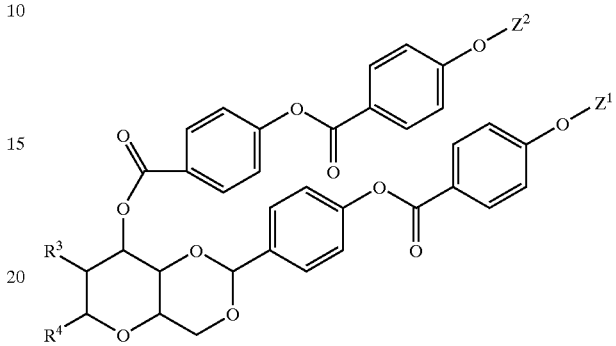

Ia in which the substituents, independently of one another, have the following meanings:

$R^3$ is hydrogen;

$R^4$ is hydrogen;

$Z^1$ and $Z^2$ are hydrogen, $C_4$–$C_{10}$-alkyl, polymerizable groups or radicals carrying polymerizable groups, where the definition of the variables $Z^1$ and $Z^2$ both in the general embodiment and in the preferred embodiment corresponds to the explanation already given above.

At least one of the radicals $Z^1$ to $Z^3$ is advantageously a polymerizable group or a radical containing a polymerizable group.

The abovementioned compounds are prepared in a manner known per se as described by U. Spohr et al., Can. J. Chem., 1993, 71(11), 1919–1927 and in DE-A-195 32 408, DE-A-44 08 171, EP-A-0 750 029 and in WO 95/16007. For further details, we refer to these specifications.

The invention also relates to chiral dopants of the general formula Ib

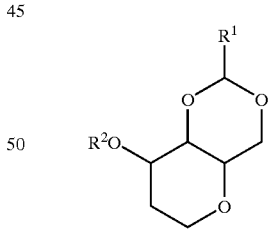

Ib in which the substituents, independently of one another, have the following meanings:

$R^1$ is $Z^1$—$Y^1$—$(A^1)_m$—$Y^2$—$M^1$—$Y^3$—$(A^2)_n$—$Y^4$—;

$R^2$ is hydrogen, $C_1$–$C_{12}$-alkyl, $C_1$–$C_{12}$-alkylcarbonyl, aryl, arylcarbonyl or $Z^2$—$Y^5$—$(A^3)_o$—$Y^6$—$M^2$—$Y^7$—$(A^4)_p$—$Y^{11}$—;

$A^1$ to $A^4$ are spacers having a chain length of from 1 to 30 carbon atoms;

$M^1$ and $M^2$ are mesogenic groups;

$Y^1$ to $Y^7$ are chemical bonds, —O—, —S—, —C(=O)—, —C(=O)—O—, —O—C(=O)—, —CH=CH—C(=O)—O—, —O—C(=O)—O—, —C(=O)—N(R)— or —(R) N—C(=O)—,
—CH$_2$O—, —O—CH$_2$—, —CH=N—, —N=CH—
or —N=N—;

$Y^{11}$ is a chemicalbond, —C(=O)—, —O—C(=O)—,
—CH=CH—C(=O)—, —(R)N—C(=O)—,
—CH$_2$— or —O—CH$_2$—;

R is hydrogen or $C_1$–$C_4$-alkyl;

$Z^1$ and $Z^2$ are hydrogen, $C_1$–$C_{12}$-alkyl, polymerizable groups or radicals carrying polymerizable groups;

m to p are 0 or 1, where the radicals $A^1$ to $A^4$, $Y^1$ to $Y^7$ and $Z^1$ and $Z^2$ may be identical or different, and where, in the case where one or more of the indices m to p are zero, at least one of the radicals Y in each case adjacent to A is a chemical bond.

Preference is given to chiral dopants in which the substituents have the following meanings:

$R^1$ is $Z^1$—$Y^1$—$(A^1)_m$—$Y^2$—$M^1$—$Y^3$—$(A^2)_n$—$Y^4$—;
$R^2$ is $Z^2$—$Y^5$—$(A^3)_o$—$Y^6$—$M^2$—$Y^7$—$(A^4)_p$—$Y^{11}$—;

$A^1$ and $A^3$ are spacers having a chain length of from 1 to 6 carbon atoms;

$Y^1$ to $Y^7$ are chemical bonds, —O—, —S—,
—C(=O)—, —C(=O)—O—, —O—C(=O)—,
—CH=CH—C(=O)—O—, —O—C(=O)—O—,
—C(=O)—N(R)— or —(R)N—C(=O)—, —CH$_2$—
O—, —O—CH$_2$—, —CH=N—, —N=CH— or
—N=N—;

$Y^{11}$ is a chemical bond, —C(=O)—, —O—C(=O)—,
—CH=CH—C(=O)—, —(R)N—C(=O)—,
—CH$_2$— or —O—CH$_2$—;

$M^1$ and $M^2$ are mesogenic radicals from the group consisting of:

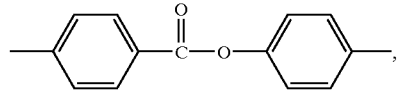

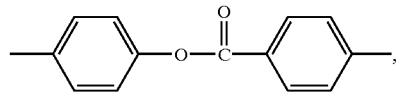

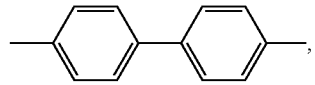

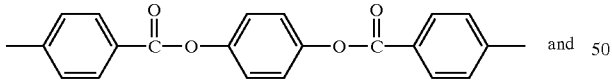 and

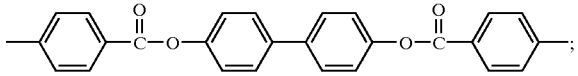;

$Z^1$ and $Z^2$ are hydrogen, $C_4$–$C_{10}$-alkyl, polymerizable groups or radicals carrying polymerizable groups;

m is 0 or 1;
n is 0;
o is 0 or 1;
p is 0,
where at least one of the radicals $Y^3$ and $Y^4$ or $Y^7$ and $Y^{11}$ is a chemical bond.

Particular preference is given to chiral dopants of the general formula Ia,

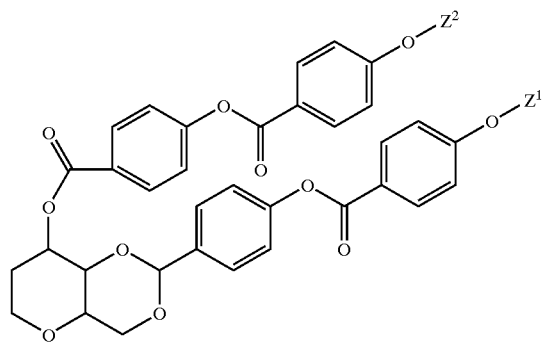

in which the substituents, independently of one another, have the following meanings:

$Z^1$ and $Z^2$ are hydrogen, $C_4$–$C_{10}$-alkyl, polymerizable groups or radicals carrying polymerizable groups.

The definition of the abovementioned variables in the general embodiment and in the preferred embodiment corresponds to the explanation already given above.

The invention also relates to cholesteric liquid-crystalline compositions comprising a) at least one chiral liquid-crystalline monomer of the general formula I

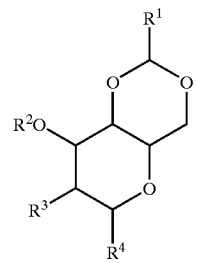

or
b) a mixture of
b$_1$) at least one achiral, liquid-crystalline, polymerizable monomer of the general formula II

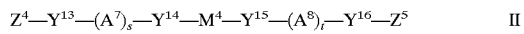

in which the variables, independently of one another, have the following meanings:

$A^7$ and $A^8$ are spacers having a chain length of from 1 to 30 carbon atoms;

$M^4$ is a mesogenic group;

$Y^{13}$ to $Y^{16}$ are chemical bonds, —O—, —S—,
—C(=O)—, —C(=O)—O—, —O—C(=O)—,
—CH=CH—C(=O)—O—, —O—C(=O)—O—,
—C(=O)—N($R^7$)— or —($R^7$)N—C(=O)—,
—CH$_2$—O—, —O—CH$_2$—, —CH=N—,
—N=CH— or —N=N—;

$R^7$ is hydrogen or $C_1$–$C_4$-alkyl;
s is 0 or 1;
t is 0 or 1;
$Z^4$ and $Z^5$
are hydrogen, $C_1$–$C_{12}$-alkyl, polymerizable groups or radicals carrying polymerizable groups,
where the radicals $A^7$ and $A^8$ and $Y^{13}$ to $Y^{16}$ may be identical or different, at least one of the variables Z⁴ or Z⁵ is a polymerizable group or a radical carrying a polymerizable group, and, in the case where one or both of the indices s and t are zero, at least one of the radicals $Y^{13}$ and $Y^{14}$ or $Y^{15}$ and $Y^{16}$ is a chemical bond, and b₂) at least one chiral liquid-crystalline monomer of the general formula I.

In the case of the achiral liquid-crystalline monomers of the formula II, the same definitions and preferred embodiments apply for the polymerizable groups $Z^4$ and $Z^5$, the bridging members $Y^{13}$ to $Y^{16}$, the spacers $A^7$ and $A^8$ and the mesogenic group $M^4$ as for the corresponding variables in the formula I.

Just as in formula I, it is also possible to link the mesogenic group directly to the radical $Z^4$ or $Z^5$. In these cases, s and/or t are 0 and $Y^{13}$ and $Y^{14}$ and/or $Y^{15}$ and $Y^{16}$ together are a chemical bond.

The mixture b) also contains at least one compound of the formula I already described above as chiral additive b₂).

Suitable dopants should have a high twisting power in order that small amounts of the dopant are sufficient to induce the helical structure. In addition, the chiral dopants should exhibit good compatibility with the liquid-crystalline compounds so that an effective interaction between these components is enabled.

The extent of twist depends in each case on the twisting power of the chiral dopant and on its concentration. The pitch of the helix and in turn also the interference wavelength is thus dependent on the concentration of the chiral dopant. It is therefore not possible to indicate a generally applicable concentration range for the dopant. The dopant is added in the amount with which the desired UV reflection is achieved.

Preferred chiral additives for b₂) are compounds of the formula I in which the substituents have the following meanings:

$R^1$ is $Z^1—Y^1—(A^1)_m—Y^2—M^1—Y^3—(A^2)_n—Y^4—$;
$R^2$ is $Z^2—Y^5—(A^3)_o—Y^6—M^2—Y^7—(A^4)_p—Y^{11}—$;
$R^3$ and $R^4$ are hydrogen;
$A^1$ and $A^3$ are spacers having a chain length of from 1 to 6 carbon atoms;
$Y^1$ to $Y^7$ are chemical bonds, —O—, —S—, —C(=O)—, —C(=O)—O—, —O—C(=O)—;
$Y^{11}$ is a chemical bond, —C(=O)— or —O—C(=O)—;
$M^1$ and $M^2$ are mesogenic radicals from the group consisting of:

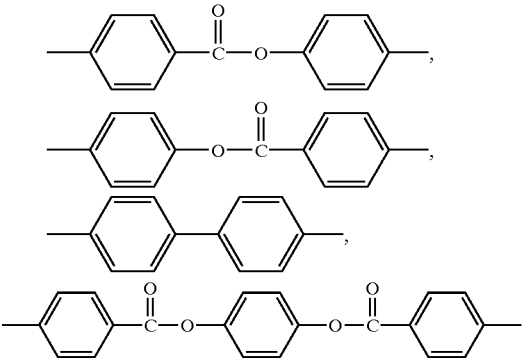

and $Z^1$ and $Z^2$ are hydrogen, $C_4$–$C_{10}$-alkyl, polymerizable groups or radicals carrying polymerizable groups;
m is 0 or 1;
n is 0;
o is 0 or 1; and
p is 0,
where at least one of the radicals $Y^3$ and $Y^4$ or $Y^7$ and $Y^{11}$ is a chemical bond.

Particularly preferred monomers II are the following structures:

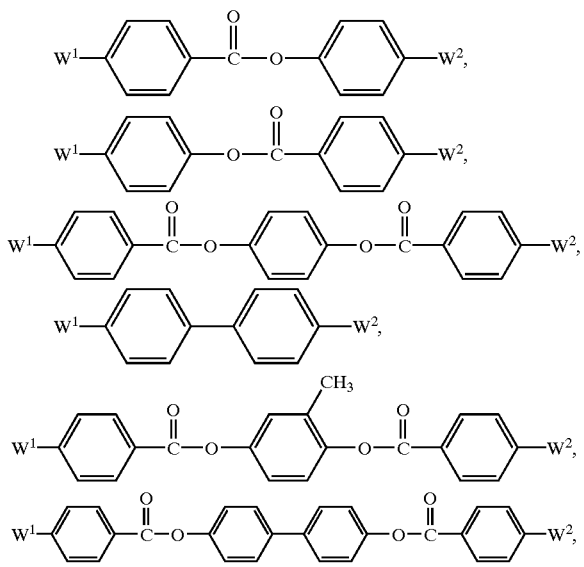

$W^1$: $CH_2=CH—C(=O)—O—(CH_2)_4—O—$,
$W^2$: $—O—(CH_2)_4—O—C(=O)—CH=CH_2$

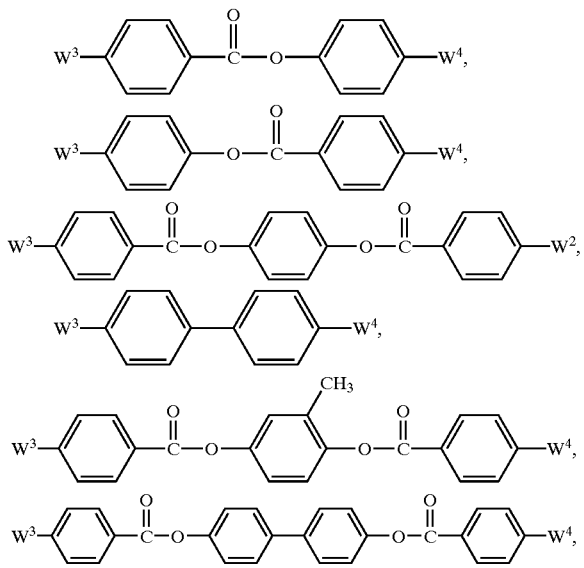

W³: CH₂=CH—C(=O)—O—(CH₂)₆—O—,
W⁴: —O—(CH₂)₆—O—C(=O)—CH=CH₂
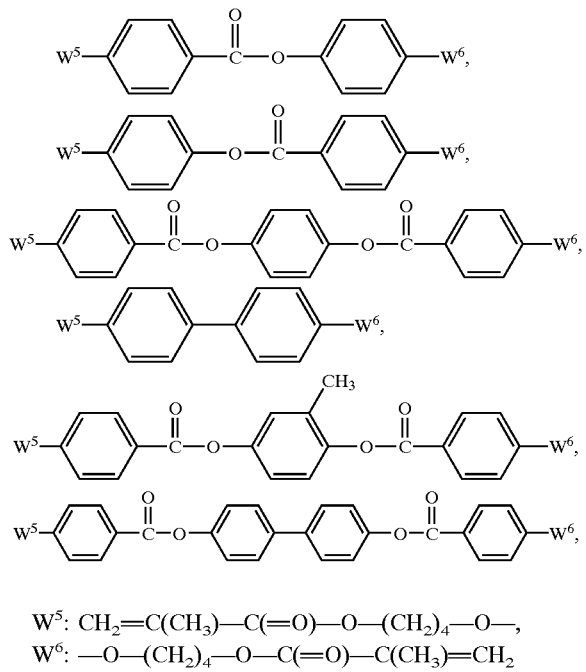
W⁵: CH₂=C(CH₃)—C(=O)—O—(CH₂)₄—O—,
W⁶: —O—(CH₂)₄—O—C(=O)—C(CH₃)=CH₂
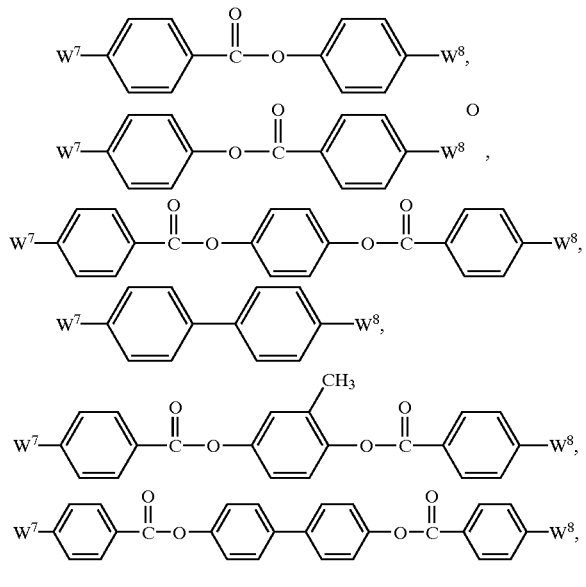
W⁷: CH₂=C(CH₃)—C(=O)—O—(CH₂)₆—O—,
W⁸: —O—(CH₂)₆—O—C(=O)—C(CH₃)=CH₂
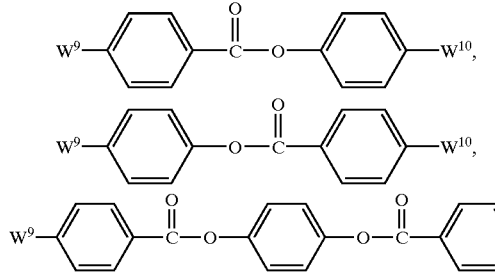
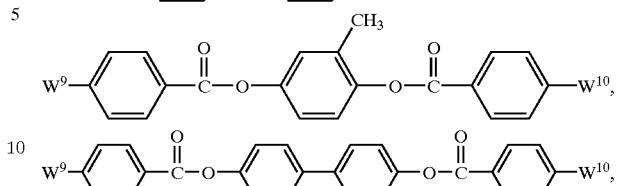
W⁹: CH₂=CH—C(=O)—O—(CH₂)₄—O—C(=O)—O—,
W¹⁰: —O—(O=)C—O—(CH₂)₄—O—C(=O)—CH=CH₂
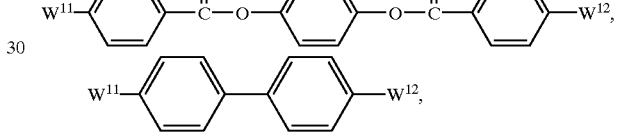
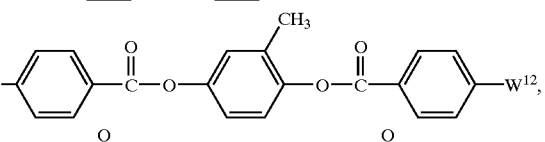
W¹¹: CH₂=CH—C(=O)—O—(CH₂)₆—O—C(=O)—O—,
W¹²: —O—(O=)C—O—(CH₂)₆—O—C(=O)—CH=CH₂
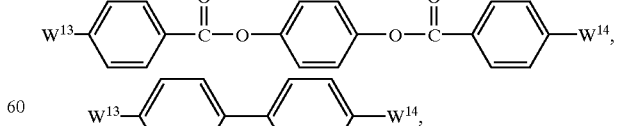

-continued
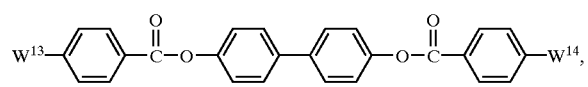
$W^{13}$: $CH_2=C(CH_3)-C(=O)-O-(CH_2)_4-O-C(=O)-O-$,
$W^{14}$: $-O-(O=)C-O-(CH_2)_4-O-C(=O)-C(CH_3)=CH_2$
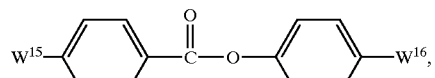
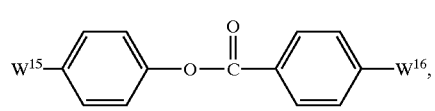
-continued
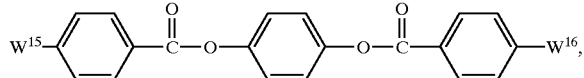
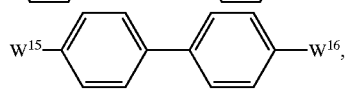
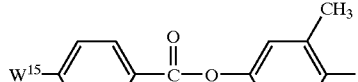
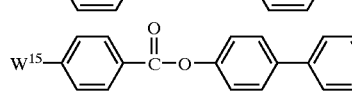
$W^{15}$: $CH_2=C(CH_3)-C(=O)-O-(CH_2)_6-O-C(=O)-O-$,
$W^{16}$: $-O-(O=)C-O-(CH_2)_6-O-C(=O)-C(CH_3)=CH_2$
Particularly preferred monomers I are the following structures:
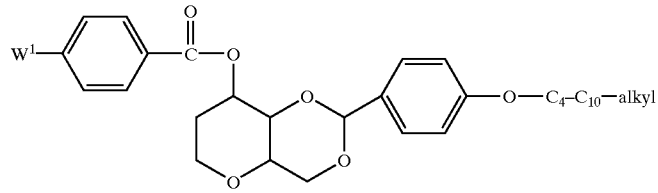
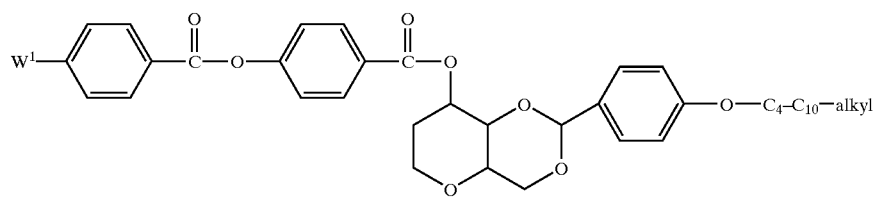
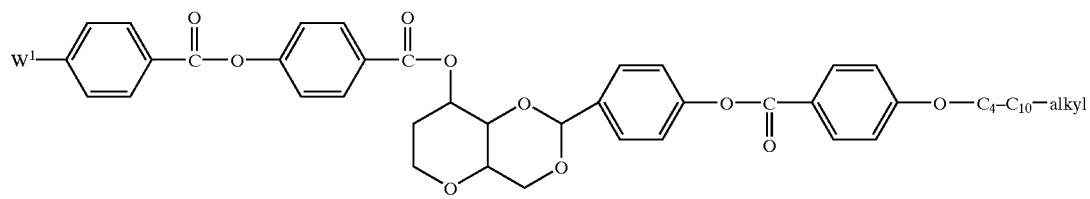
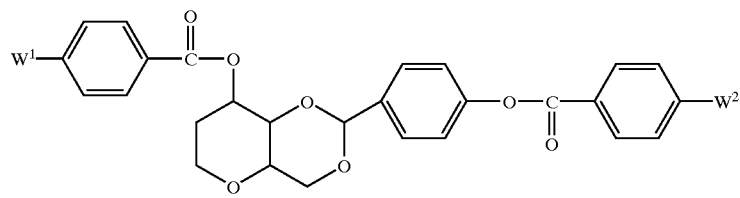
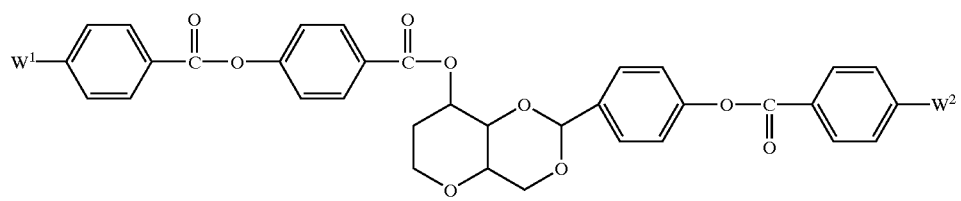

W¹: CH₂=CH—C(=O)—O—(CH₂)₄—O—
W²: —O—(CH₂)₄—O—C(=O)—CH=CH₂
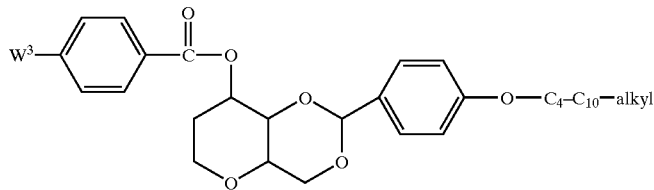
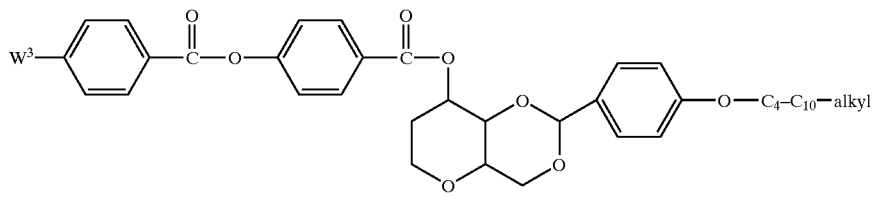
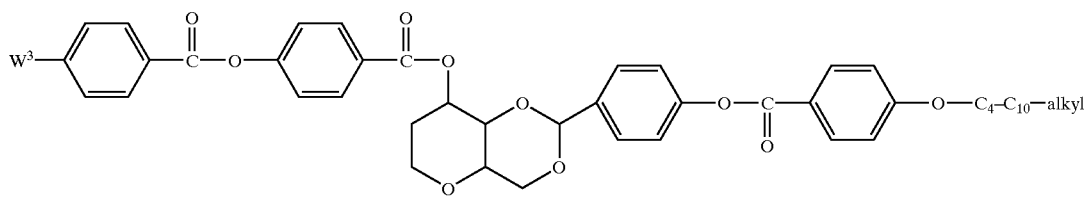
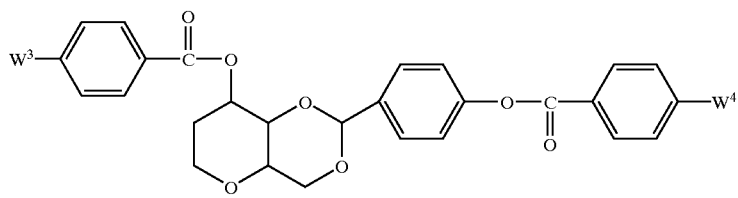
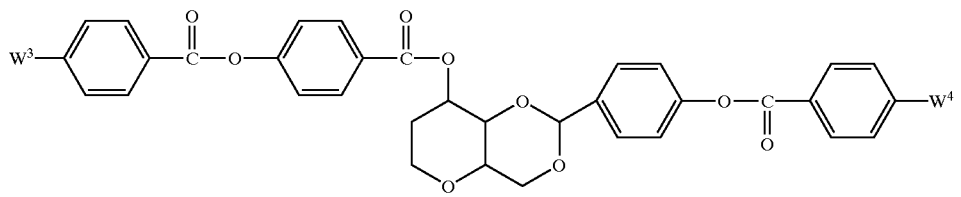
W³: CH₂=CH—C(=O)—O—(CH₂)₆—O—
W⁴: —O—(CH₂)₆—O—C(=O)—CH=CH₂
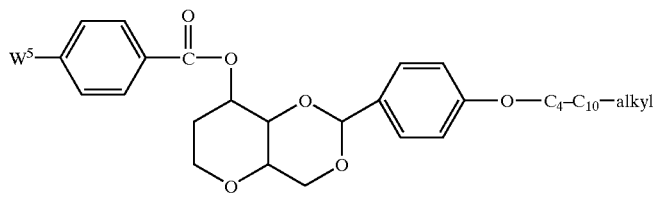
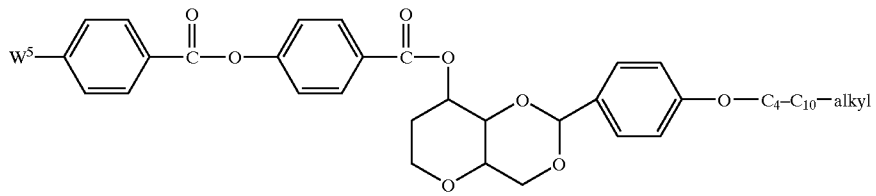

-continued
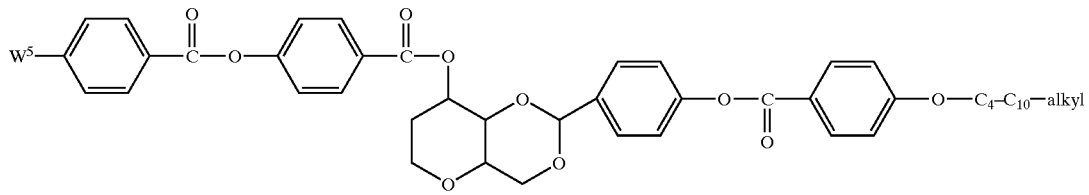
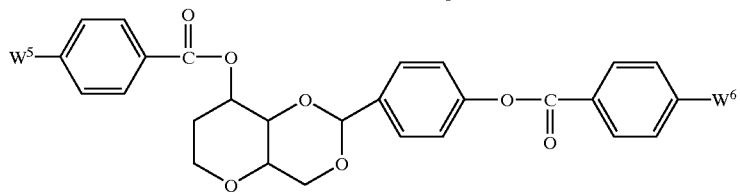
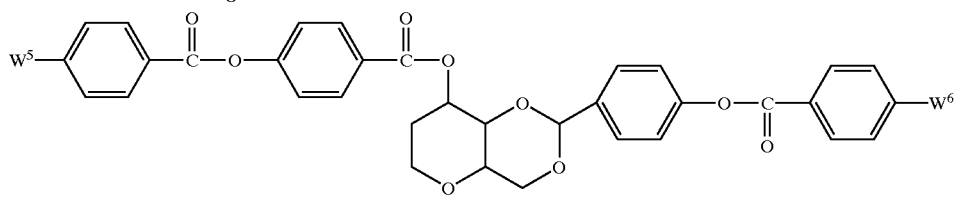
$W^5$: $CH_2=C(CH_3)-C(=O)-O-(CH_2)_4-O-$,
$W^6$: $-O-(CH_2)_4-O-C(=O)-C(CH_3)=CH_2$
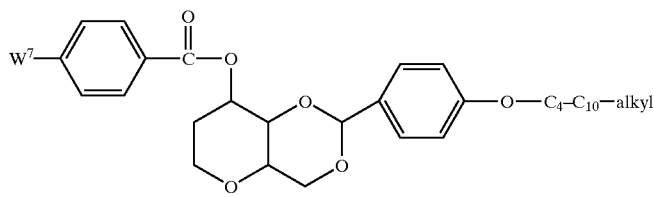
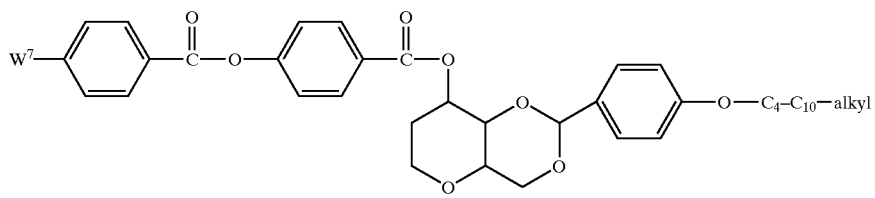
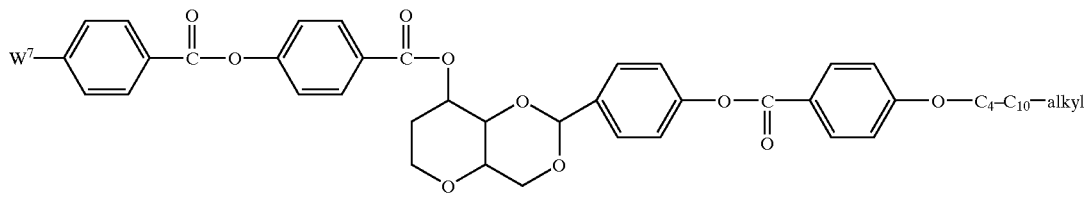
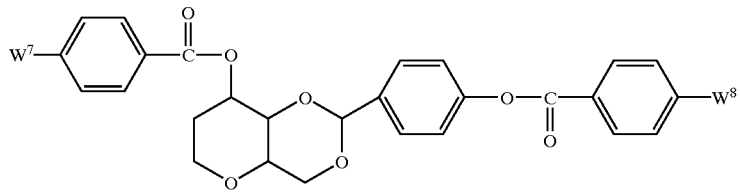
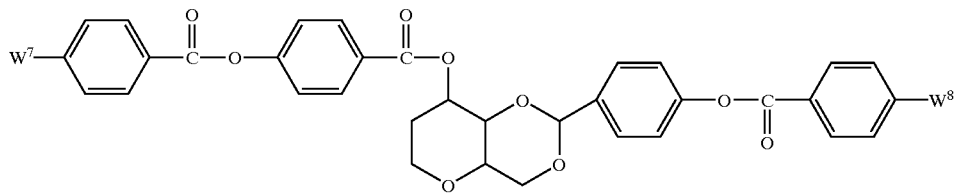

W⁷: $CH_2=C(CH_3)-C(=O)-O-(CH_2)_6-O-$,
W⁸: $-O-(CH_2)_6-O-C(=O)-C(CH_3)=CH_2$
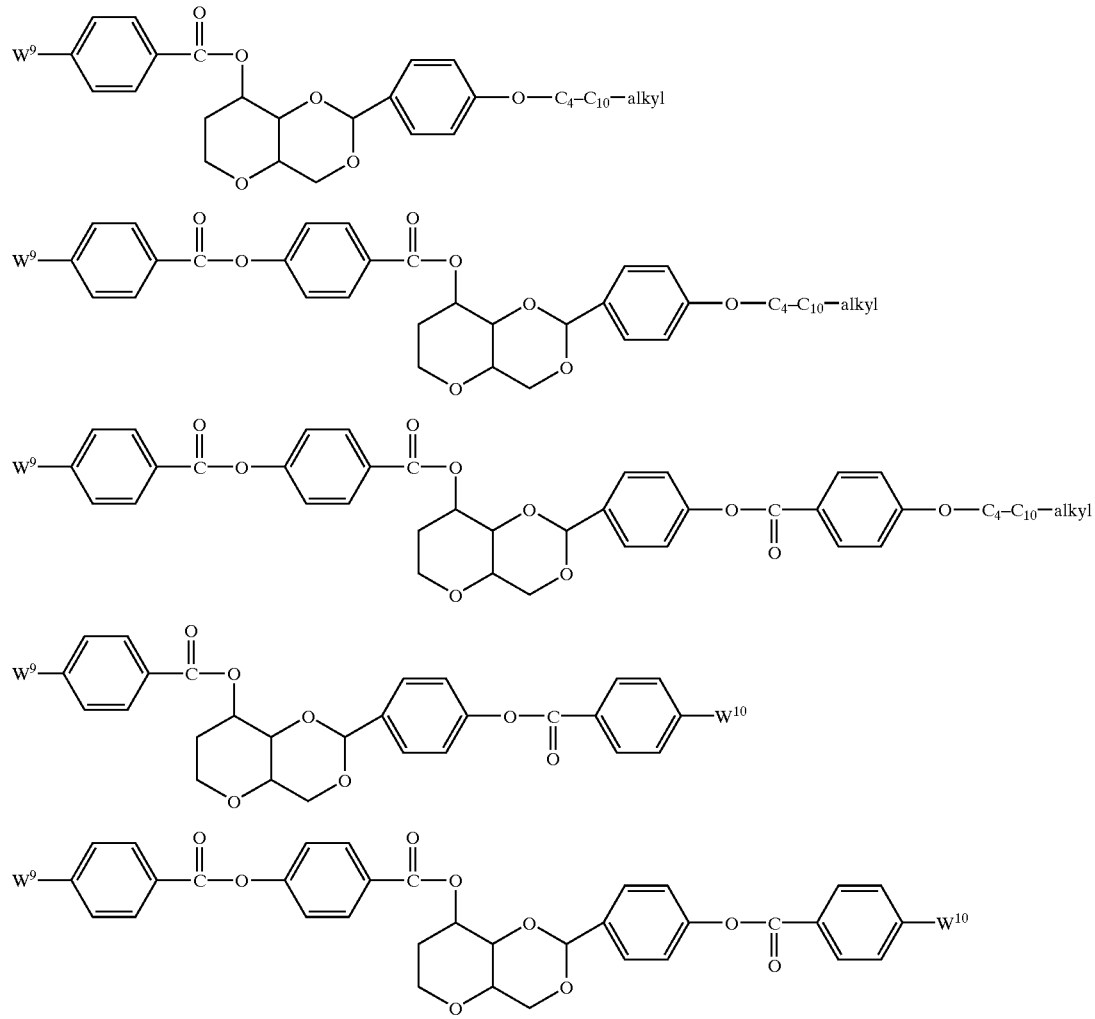
W⁹: $CH_2=CH-C(=O)-O-(CH_2)_4-O-C(=O)-O-$
W¹⁰: $-O-(O=)C-O-(CH_2)_4-O-C(=O)-CH=CH_2$
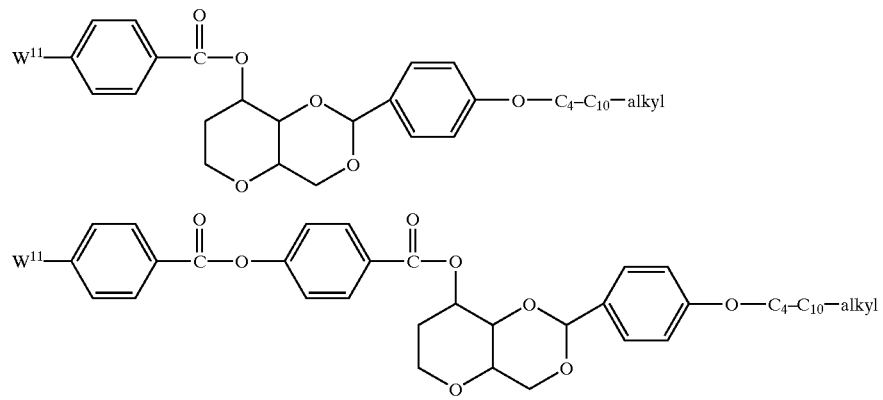

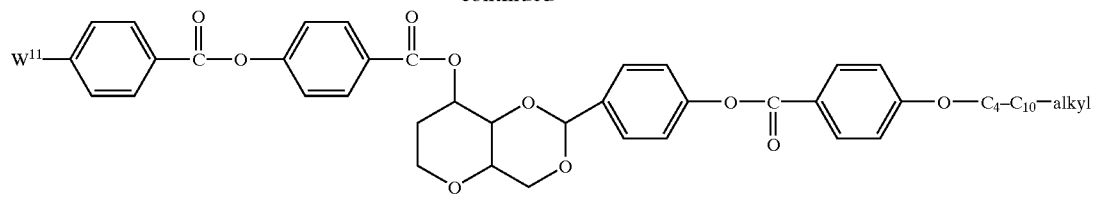
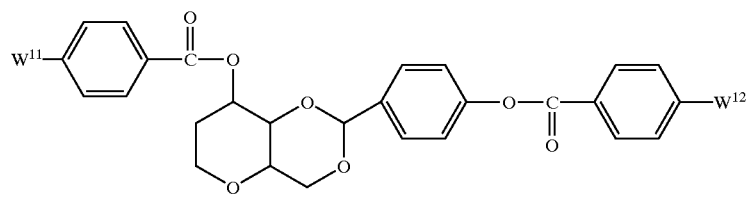
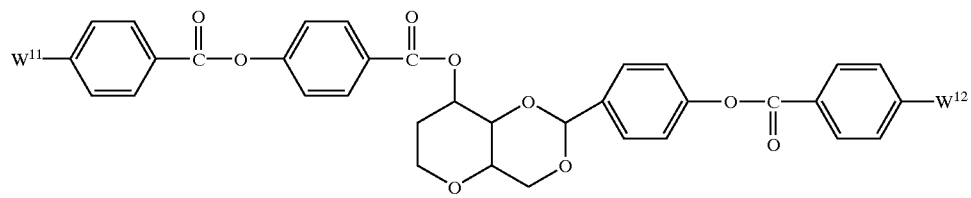
$W^{11}$: $CH_2$=CH—C(=O)—O—$(CH_2)_6$—O—C(=O)—O—
$W^{12}$: —O—(O=)C—O—$(CH_2)_6$—O—C(=O)—CH=$CH_2$
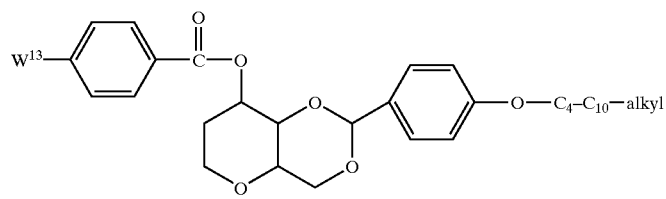
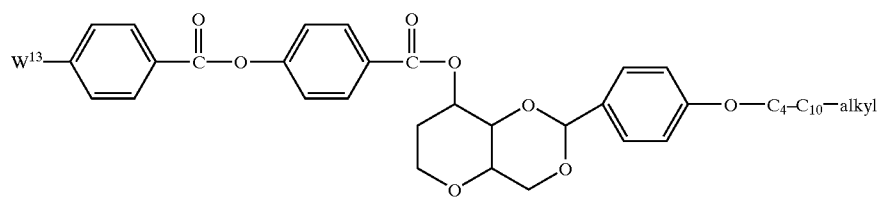
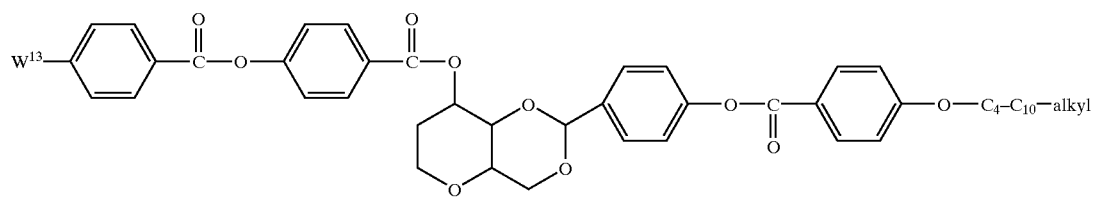
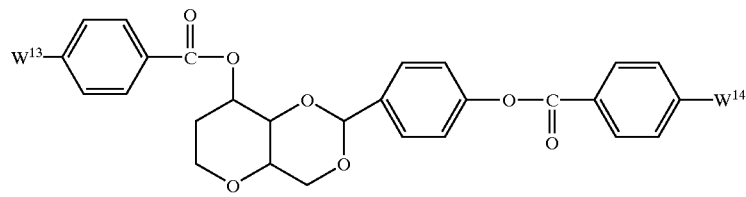

-continued

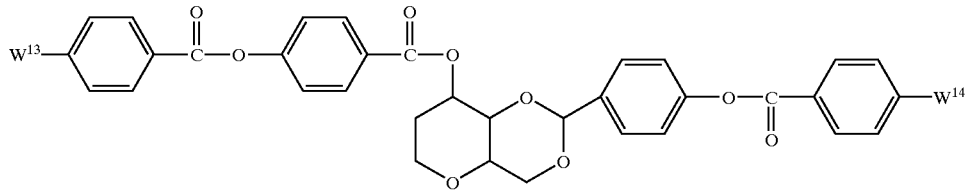

$W^{13}$: $CH_2=C(CH_3)-C(=O)-O-(CH_2)_4-O-C(=O)-O-$,
$W^{14}$: $-O-(O=)C-O-(CH_2)_4-O-C(=O)-C(CH_3)=CH_2$

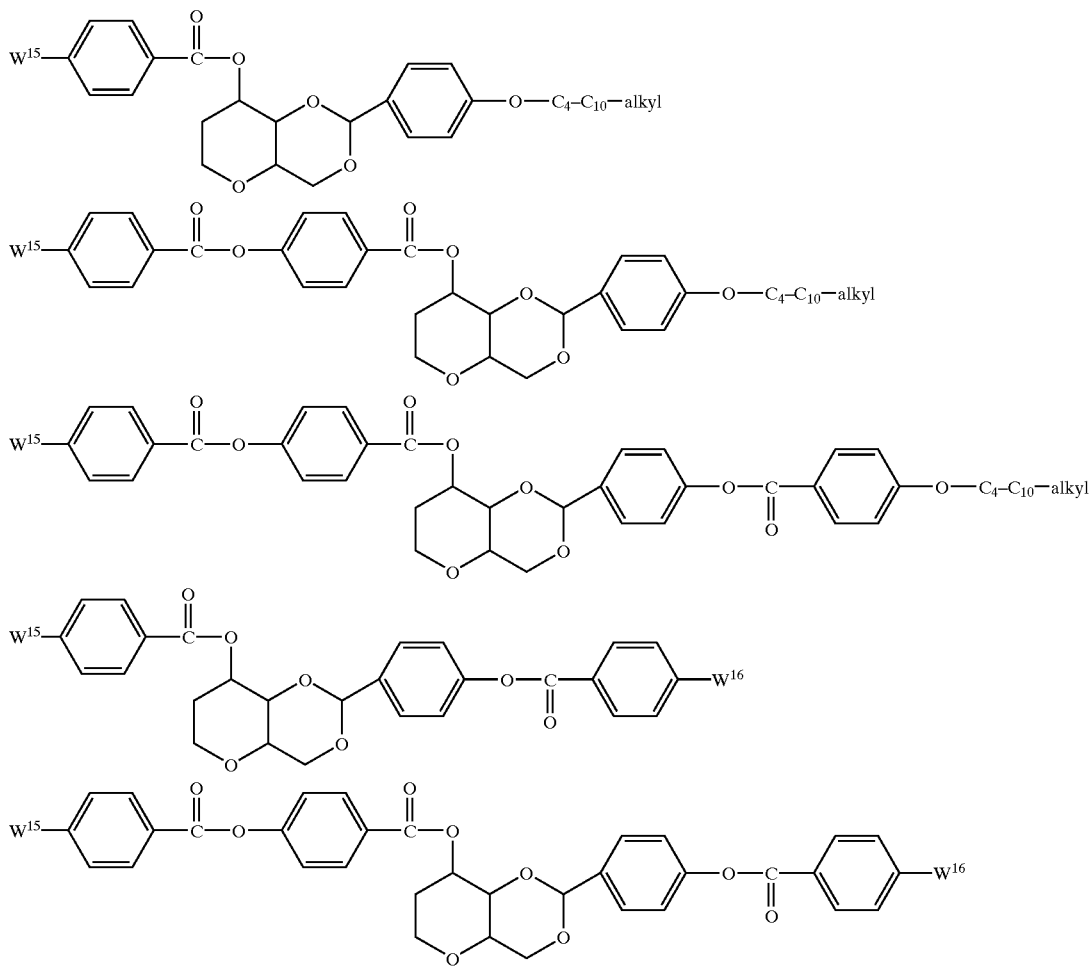

$W^{15}$: $CH_2=C(CH_3)-C(=O)-O-(CH_2)_6-O-C(=O)-O-$,
$W^{16}$: $-O-(O=)C-O-(CH_2)_6-O-C(=O)-C(CH_3)=CH_2$

The weight ratios between components II and I are in the range from 99:1 to 40:60, preferably in the range from 99:1 to 70:30, particularly preferably from 98:2 to 85:15.

A particular characteristic of the above cholesteric liquid-crystalline compositions is that they reflect left-handed circular-polarized light.

Use of the cholesteric liquid-crystalline compositions according to the invention in cosmetic and pharmaceutical preparations:

The light protection agents used in cosmetic and pharmaceutical preparations have the job of eliminating or at least reducing harmful effects of sunlight on the human skin. In addition, however, these light protection agents also serve to protect other ingredients against destruction or degradation by UV radiation. In hair-cosmetic formulations, the aim is to reduce damage to keratin fibers by UV rays.

The sunlight reaching the earth'surface has a UV-B component (280 to 320 nm) and a UV-A component (>320 nm) directly adjacent to the visible region of light. The effect on the human skin is particularly evident in the case of UV-B radiation in the form of sunburn. Accordingly, the industry offers a relatively large number of substances which absorb UV-B radiation and thus prevent sunburn.

Dermatological investigations have shown that UV-A radiation is also entirely capable of causing skin damage and allergies, for example by damaging the keratin or elastin. This results in a reduction in elasticity and water storage capacity of the skin, i.e. the skin becomes less flexible and tends to wrinkle. The strikingly high frequency of skin cancer in regions of strong sunlight shows that damage to genetic information in the cells is apparently also caused by sunlight, especially by UV-A radiation. All this knowledge therefore makes the development of efficient filter substances for the UV-A and UV-B regions appear necessary.

In addition to known UV absorbers, for example 2-ethylhexyl 4-methoxycinnamate and 3-(4'-methyl) benzylidenebornan-2-one, light protection agents which, in the form of pigments, reflect or absorb UV rays are frequently also used in cosmetic and pharmaceutical formulations. The most important of these pigments are titanium dioxide and zinc oxide. At high concentrations, pigments can achieve full screening of the skin. However, the particles then reflect not only UV radiation, but also visible light, causing the frequently undesired strong inherent coloration of pigment-containing preparations.

Whereas titanium dioxide pigments with coarse particles (particle size>500 nm) have a comparable action in the UV-B and UV-A regions, the spectrum of action shifts toward the UV-B with decreasing particle size in the case of finely divided material. This shows that the absorption/reflection characteristics are directly dependent on the size and distribution of the particles. Balanced UV-B and UV-A protection therefore requires certain particle-size distributions.

It has been found to be disadvantageous on use of the abovementioned pigments that agglomeration, aggregation and/or separation of the pigment particles frequently occurs during storage of the cosmetic or pharmaceutical light protection agent formulations. The consequence of the modified optical properties can be a drastically reduced light protection action.

As an alternative to the abovementioned pigments, DE-A-196 19 460 describes the use of liquid-crystal mixtures having a cholesteric phase comprising a) liquid-crystalline organosiloxanes containing dianhydrohexitol derivatives as chiral groups, and b) chiral monomeric additives which induce the same helicity as the respective liquid-crystalline organosiloxanes, for the production of UV protection layers, in the form of films or flakes, which are suitable for cosmetic purposes. The liquid-crystal mixtures described here have the disadvantage that they can be converted into pigments only unsatisfactorily owing to their high viscosity.

DE-A-196 29 761 describes cosmetic or pharmaceutical preparations comprising polyorganosiloxane pigments having a viewing angle-dependent color. The pigments are at least one oriented, crosslinked substance of a liquid-crystalline structure with a chiral phase. Although the pigments disclosed here in the cosmetic and pharmaceutical formulations have certain absorption properties in the UV region, they have the disadvantage for certain applications of being colored compounds, whose range of applications is consequently restricted. However, there is very frequently a demand for precisely those cosmetic and pharmaceutical preparations by means of which UV protection is achieved, but in which coloration of the preparation is undesired.

The present invention therefore also relates to the use of the abovementioned cholesteric liquid-crystalline compositions as UV filters in cosmetic and pharmaceutical preparations for protecting the human skin or human hair against sunlight, alone or together with UV-absorbent compounds which are known per se for cosmetic and pharmaceutical preparations.

The cholesteric liquid-crystalline compositions used which are preferred for use as UV filters in cosmetic and pharmaceutical preparations comprise a mixture of at least one achiral; liquid-crystalline, polymerizable monomer of the formula II and at least one chiral polymerizable monomer of the formula I.

For the novel use of the abovementioned cholesteric liquid-crystalline compositions a) and b) as UV filters in cosmetic and pharmaceutical preparations, the components of the formulae I and II present in these compositions can be incorporated directly into the cosmetic and pharmaceutical preparations.

Preferably, however, the cholesteric liquid-crystalline compositions used in accordance with the invention are employed in the form of pigments. These pigments are obtainable by converting the monomers I and II present in the cholesteric liquid-crystalline compositions into highly crosslinked polymers having a frozen liquid-crystalline order structure with the aid of their polymerizable groups by free-radical or ionic polymerization processes, which can be initiated by a photochemical reaction.

The preparation of these pigments is known and is described in detail in, inter alia, German Application P 19738369.6.

In addition, an overview of processes for the photochemical crosslinking of oriented starting materials is given in C. G. Roffey, Photopolymerisation of Surface Coatings, (1982) John Willey & Sons, Chichester, pp. 137 to 208.

In a preferred embodiment, the three-dimensionally crosslinkable, polymerizable monomers are applied to a substrate, crosslinked on this substrate and detached from the substrate after the crosslinking.

The cholesteric liquid-crystalline compositions which have been crosslinked to give a film can, after the polymerization, be comminuted to the particle size desired in each case by grinding. Depending on the desired application and the type of cosmetic or pharmaceutical formulation, particles having a diameter of from 1 to 1000 $\mu$m can be produced. Preferred particle sizes are in the range from 1 to 100 $\mu$m, particularly preferably in the range from 15 to 50 $\mu$m.

The thickness of the pigments is from 1 to 100 $\mu$m, preferably from 1 to 50 $\mu$m, particularly preferably from 1.5 to 10 $\mu$m.

The cholesteric liquid-crystalline compositions a) and b) which are suitable as starting substances for the preparation of the pigments have a twisted structure with a pitch corresponding to a light wavelength of up to 450 nm. As shown in the preferred embodiments b), these twisted structures having a defined pitch can be obtained from nematic structures $b_1$) by adding a chiral substance $b_2$). The nature and proportion of the chiral substance determine the pitch of the twisted structure and thus the wavelength of the reflected light. Depending on the chirality of the optically active additives employed, the twist of the structure can be either left-handed or right-handed.

So-called broad-band reflectors can be produced by simply mixing a plurality of the cholesteric liquid-crystalline pigments to be used in accordance with the invention, each with different UV reflection maxima.

In addition, it is possible to achieve complete reflection of the UV rays by mixing at least two different pigments in the cholesteric liquid-crystalline compositions a) and/or b) with opposite twist (helicity). Pigments having such cholesteric liquid-crystalline structures of opposite twist are obtainable, for example, by adding the individual mirror-image isomers (enantiomers) or diastereomers of the chiral additives $b_2$) to the achiral, liquid-crystalline, polymerizable monomer $b_1$). The pitch of the structures of opposite twist can be identical or different.

It is also possible firstly to mix the cholesteric liquid-crystalline compositions a) or b) of opposite twist and then to convert the mixture into the above-described pigments by the abovementioned crosslinking and to employ the pigments as UV reflectors in cosmetic and pharmaceutical formulations.

Besides the abovementioned mixtures of cholesteric liquid-crystalline pigments, it is also possible to prepare multilayer pigments whose individual layers comprise different three-dimensionally crosslinked cholesteric liquid-crystalline compositions to be used in accordance with the invention. The design of such multilayer pigments can be varied widely. Thus, inter alia, individual layers of crosslinked cholesteric liquid-crystalline compositions of opposite twist or individual layers of crosslinked cholesteric liquid-crystalline compositions having the same twist direction, but different pitch and thus different reflection properties, can be applied one on top of the other.

Preference is given to so-called three-layer pigments, in which the two outer layers each consist of at least one of the crosslinked, cholesteric liquid-crystalline compositions to be used in accordance with the invention, and the middle layer can comprise, for example, a binder matrix, in which, in addition, a further UV absorber may be incorporated. Details on the preparation, properties and further constituents of such multilayered, cholesteric pigments are given in German Patent Application P 19738368.8.

The invention thus also relates to the above-described pigments, in particular multilayer pigments, comprising the cholesteric liquid-crystalline compositions mentioned at the outset.

An advantage of the pigments used in accordance with the invention is that their composition can be customized so that the desired UV reflection can be achieved using these pigments without exhibiting any inherent color (in the visible region).

A further advantage of the pigments consists in their physical properties. Owing to their low density (compared, for example, with $TiO_2$), the pigments can readily be incorporated into emulsions without any aggregation or separation of pigment particles.

The pigments to be used in accordance with the invention can be incorporated into the cosmetic and pharmaceutical preparations by simple mixing.

The present invention furthermore relates to cosmetic and pharmaceutical preparations comprising from 0.1 to 20% by weight, preferably from 0.5 to 10% by weight, particularly preferably from 1 to 7% by weight, based on the total amount of the cosmetic and pharmaceutical preparation, of one or more of the cholesteric liquid-crystalline compositions comprising a) at least one chiral, liquid-crystalline, polymerizable monomer of the general formula I, by means of which a cholesteric liquid-crystalline phase with a pitch of less than 450 nm can be achieved, or b) a mixture of at least one achiral, liquid-crystalline, polymerizable monomer of the general formula II and at least one chiral, liquid-crystalline, polymerizable monomer of the general formula I, by means of which a cholesteric liquid-crystalline phase with a pitch of less than 450 nm can be achieved, together with compounds which absorb in the UV-A and UV-B region which are known per se for cosmetic and pharmaceutical preparations, as light protection agents. The variables in the formulae I and II and the class of the chiral additives employed correspond, in both their general and preferred embodiments, to the explanations already outlined above.

Preference is given to those of the abovementioned cosmetic and pharmaceutical preparations which comprise the cholesteric liquid-crystalline compositions to be used in accordance with the invention in the form of the pigments described above, in particular in the form of multilayered pigments.

The cosmetic and pharmaceutical preparations containing light protection agents are generally based on a carrier comprising at least one oil phase. However, preparations based exclusively on water are also possible if compounds having hydrophilic substituents are used. Accordingly, oils, oil-in-water and water-in-oil emulsions, creams and pastes, compositions for lip protection sticks and fat-free gels are suitable.

Sun protection preparations of this type can accordingly be in liquid, pasty or solid form, for example as water-in-oil creams, oil-in-water creams and lotions, aerosol foam creams, gels, oils, fat sticks, powders, sprays or alcoholic/aqueous lotions.

Conventional oil components in cosmetics are, for example, paraffin oil, glyceryl stearate, isopropyl myristate, diisopropyl adipate, stearyl 2-ethylhexanoate, hydrogenated polyisobutene, vaseline, caprylic acid/caproic acid triglycerides, microcrystalline wax, lanolin and stearic acid.

Conventional cosmetic auxiliaries which are suitable as additives are, for example, coemulsifiers, fats and waxes, stabilizers, thickeners, biogenic active ingredients, film formers, fragrances, colorants, pearlescent agents, preservatives, pigments, electrolytes (for example magnesium sulfate) and pH regulators. Preferred coemulsifiers are known W/O and also O/W emulsifiers, for example polyglycerol esters, sorbitan esters and partially esterified glycerides. Typical examples of fats are glycerides; waxes include beeswax, paraffin wax and microwaxes, if desired in combination with hydrophilic waxes. Suitable stabilizers are metal salts of fatty acids, for example magnesium stearate, aluminum stearate and/or zinc stearate. Examples of suitable thickeners are crosslinked polyacrylic acids and derivatives thereof, polysaccharides, in particular xanthan gum, guar guar, agar agar, alginates and tyloses, carboxymethylcellulose and hydroxyethylcellulose, furthermore fatty alcohols, monoglycerides and fatty acids, polyacrylates, polyvinyl alcohol and polyvinylpyrrolidone. The term biogenic active ingredients is taken to mean, for example, plant extracts, albumen hydrolyzates and vitamin complexes. Customary film formers are, for example, hydrocolloids, such as chitosan, microcrystalline chitosan and quaternized chitosan, polyvinylpyrrolidone, vinylpyrrolidone-vinyl acetate copolymers, acrylic acid polymers, quaternary cellulose derivatives and similar compounds. Examples of suitable preservatives are formaldehyde solution, p-hydroxybenzoate and sorbic acid. Examples of suitable pearlescent agents are glycol distearic esters, such as ethylene glycol distearate, but also fatty acids and fatty acid monoglycol esters. Suitable colorants are the substances which are suitable and approved for cosmetic purposes, as listed, for example, in the publication "Kosmetische Färbemittel" [Cosmetic Colorants] by the Farbstoffkommission der Deutschen Forschungsgemeinschaft, published by Verlag Chemie, Weinheim, 1984. These colorants are usually employed in concentrations of from 0.001 to 0.1% by weight, based on the total mixture.

The preparations according to the invention advantageously comprise one or more antioxidants. Favorable, but nevertheless optional antioxidants are all natural, synthetic and/or partially synthetic antioxidants which are suitable or customary for cosmetic and/or dermatological applications.

The antioxidants are particularly advantageously selected from the group consisting of:

amino acids (for example glycine, histidine, tyrosine and tryptophan) and derivatives thereof, imidazoles (for example urocaninic acid) and derivatives thereof, peptides, such as D,L-carnosine, D-carnosine, L-carnosine and derivatives thereof (for example anserine), carotenoids (for example β-carotene and lycopine) and derivatives thereof, lipoic acid and derivatives thereof (for example dihydrolipoic acid), aurothioglucose, propylthiouracil and other thio compounds (for example thioredoxin, glutathione, cysteine, cystine, cystamine and the glycosyl, N-acetyl, methyl, ethyl, propyl, amyl, butyl, lauryl, palmitoyl, oleyl, γ-linoyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (for example buthionine sulfoximine, homocysteine sulfoximine, buthionine sulfone, penta-, hexa- and heptathionine sulfoximine) in very small compatible dosages (for example pmol to µmol/kg), furthermore (metal) chelators (for example α-hydroxy fatty acids, palmitic acid, phytic acid and lactoferrin), α-hydroxy acids (for example citric acid, lactic acid and malic acid), humic acid, bile acid, bile extracts, biliburin, biliverdin, EDTA, EGTA and derivatives thereof, unsaturated fatty acids and derivatives thereof (for example γ-linolenic acid, linoleic acid and oleic acid), folic acid and derivatives thereof, (for example 5-methyltetrahydrofolic acid), ubiquinone and ubiquinol and derivatives thereof, vitamin C and derivatives thereof (for example ascorbyl palmitate, ascorbyl phosphates and ascorbyl acetates), tocopherols and derivatives thereof (for example tocopheryl acetate and tocotrienol), vitamin A and derivatives (for example vitamin A palmitate), rutinic acid and derivatives thereof, ferulic acid and derivatives thereof, butylhydroxytoluene, butylhydroxyanisol, nordihydroguaiacic acid, nordihydroguaiaretic acid, trihydroxybutyrophenone, uric acid and derivatives thereof, stilbenes and derivatives thereof.

The total proportion of the auxiliaries and additives can be from 1 to 80% by weight, preferably from 6 to 40% by weight, and the non-aqueous component ("active substance") can be from 20 to 80% by weight, preferably from 30 to 70% by weight, based on the preparation. The preparation can be prepared in a manner known per se, for example by hot, cold, hot/cold or PIT emulsification. These are purely mechanical processes, with no chemical reaction.

Finally, further UV-absorbent substances known per se can also be used as long as they are stable in the overall system of the combination of UV filters to be used in accordance with the invention.

The majority of the light protection agents in the cosmetic and pharmaceutical preparations serving to protect the human epidermis consist of compounds which absorb UV light in the UV-B region, i.e. in the region from 280 to 320 nm. For example, the proportion of cholesteric liquid-crystalline compositions to be used in accordance with the invention is from 10 to 90% by weight, preferably from 20 to 70% by weight, based on the total amount of UV-B- and UV-A-absorbent substances.

Suitable UV filter substances which can be used in combination with the cholesteric liquid-crystalline compositions to be used in accordance with the invention are any desired UV-A and UV-B filter substances. The following may be mentioned by way of example:

| No. | Substance | CAS No. (=acid) |
|---|---|---|
| 1 | 4-Aminobenzoic acid | 150-13-0 |
| 2 | 3-(4'-Trimethylammonium)benzylidene-bornan-2-one methylsulfate | 52793-97-2 |
| 3 | 3,3,5-Trimethylcyclohexyl salicylate (homosalate) | 118-56-9 |
| 4 | 2-Hydroxy-4-methoxybenzophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)bis(7,7-dimethyl-2-oxobicyclo[2.2.1]heptane-1-methanesulfonic acid) and its salts | 90457-82-2 |
| 7 | Polyethoxyethyl 4-bis(polyethoxy)amino-benzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | 2-Isoamyl 4-methoxycinnamate | 71617-10-2 |
| 11 | 2-Ethylhexyl 4-methoxycinnamate | 5466-77-3 |
| 12 | 2-Hydroxy-4-methoxybenzophenone-5-sulfonic acid (sulisobenzone) and its sodium salt | 4065-45-6 |
| 13 | 3-(4'-Methyl)benzylidenebornan-2-one | 36861-47-9 |
| 14 | 3-Benzylidenebornan-2-one | 15087-24-8 |
| 15 | 1-(4'-Isopropylphenyl)-3-phenylpropane-1,3-dione | 63250-25-9 |
| 16 | 4-Isopropylbenzyl salicylate | 94134-93-7 |
| 17 | 3-Imidazol-4-yl-acrylic acid and its ethyl ester | 104-98-3 |
| 18 | Ethyl 2-cyano-3,3-diphenylacrylate | 5232-99-5 |
| 19 | 2'-Ethylhexyl 2-cyano-3,3-diphenylacrylate | 6197-30-4 |
| 20 | Menthyl-o-aminobenzoates (5-methyl-2-(1-methylethyl)-2-aminobenzoates) | 134-09-8 |
| 21 | Glyceryl p-aminobenzoate (1-glyceryl 4-aminobenzoate) | 136-44-7 |
| 22 | 2,2'-Dihydroxy-4-methoxybenzophenone (dioxybenzone) | 131-53-3 |
| 23 | 2-Hydroxy-4-methoxy-4-methylbenzo-phenone (Mexonone) | 1641-17-4 |
| 24 | Triethanolamine salicylate | 2174-16-5 |
| 25 | Dimethoxyphenylglyoxalic acid (sodium 3,4-dimethoxyphenylglyoxalate) | 4732-70-1 |
| 26 | 3-(4'-Sulfo)benzylidenebornan-2-one and its salts | 56039-58-8 |
| 27 | 4-tert-Butyl-4'-methoxydibenzoylmethane | 70356-09-1 |
| 28 | 2,2',4,4'-Tetrahydroxybenzophenone | 131-55-5 |
| 29 | 4,4'-[[6-[[4-[[(1,1-dimethylethyl)amino]-carbonyl]phenyl]amino]-1,3,5-triazin-2,4-diyl]diimino]bis-, bis(2-ethylhexyl)benzoate | 154702-15-5 |
| 30 | 2-(2H-Benzotriazol-2-yl)-4-methyl-6-[2-methyl-3-[1,3,3,3-tetramethyl-1-[(trimethyl-silyl)oxy]disiloxanyl]propyl]phenol | 155633-54-8 |
| 31 | Dimethicon diethyl benzal malonate | 207574-74-1 |
| 32 | Bis[2-hydroxy-5-tert-octyl-3-(benzotriazol-2-yl)phenyl]methane (bisoctyltriazone) | 103597-45-1 |
| 33 | 1H-benzimidazole-4,6-disulfonic acid, 2,2'-(1,4-phenylene)bis-, disodium salt (benzimidazylate) | 180898-37-7 |
| 34 | Phenol, 2,2'-[6-(4-methoxyphenyl)-1,3,5-triazin-2,4-diyl]bis[5-[(2-ethylhexyl)oxy]]-(aniso triazine) | 187393-00-6 |
| 35 | 2,4,6-Trianiline-(o-carbo-2'-ethylhexyl-1'-oxy)-1,3,5-triazine | 88122-99-0 |

Finally, mention should also be made of micronized pigments, such as titanium dioxide and zinc oxide.

For protection of human hair against UV rays, the cholesteric liquid-crystalline compositions a) and/or b) used in accordance with the invention can be incorporated into shampoos, lotions, gels, hair sprays, aerosol foam creams or emulsions in concentrations of from 0.1 to 20% by weight, preferably from 0.5 to 10% by weight, particularly preferably from 1 to 7% by weight. The respective formulations can be used, inter alia, for washing, coloring and styling hair.

The compositions to be used in accordance with the invention are generally distinguished by a particularly high reflection capacity in the region of UV-A and UV-B radiation with a sharp band structure. They can furthermore readily be incorporated into cosmetic and pharmaceutical formulations. In addition, they are particularly distinguished by their high photostability, and the preparations prepared therewith by their pleasant feel on the skin.

The UV filter action of the cholesteric liquid-crystalline compositions a) and/or b) used in accordance with the invention can also be utilized for stabilization of active ingredients and auxiliaries in cosmetic and pharmaceutical formulations.

The examples below are intended to illustrate the chiral dopants, their preparation and use in greater detail.

EXAMPLE 1

Tri-O-acetyl-D-arabino-1,5-anhydro-2-deoxy-hexitol (1)

1

10.0 g (36.5 mmol) of 3,4,6-tri-O-acetyl-D-glucal were dissolved in 140 ml of ethyl acetate/ethanol (1:1), a spatula tip of palladium catalyst (Pd/C 10%) was added, and the mixture was stirred at room temperature under a hydrogen atmosphere. When the hydrogenation was complete, the catalyst was filtered off, and the solvent mixture was removed under reduced pressure.

Yield: 10 g (36.5 mmol, 100%), colorless syrup

1H-NMR (400 MHz, CDCl$_3$): δ=5.04–4.94 (m, 2H, H-3, H-4), 4.24 (dd, 1H, H-6a), 4.10 (dd, 1H, H-6b), 4.04 (ddd, 1H, H-1eq), 3.56–3.48 (m, 2H, H-1ax, H-5), 2.13–2.07 (m, 4H, H-2eq, 3×H-OAc), 2.04 (s, 3H, 3×H-OAc), 2.03 (s, 3H, 3×H-OAc), 1.83 (mc, 1H, H-2ax) ppm; $J_{6a,6b}$=12.4, $J_{5,6a}$=5.0, $J_{5,6b}$=2.0, $J_{1eq,2ax}$=5.0, $J_{1eq,2eq}$=1.5 Hz.

EXAMPLE 2

D-arabino-1,5-anhydro-2-deoxy-hexitol (2)

2

9.5 g (34.7 mmol) of 1 were dissolved in 150 ml of anhydrous methanol, and sodium methoxide was added until the mixture was basic. After the mixture had been stirred at room temperature for 12 hours, it was neutralized using acidic ion exchanger (Amberlite IR 120 H$^+$-form) and filtered, and the solvent was removed under reduced pressure.

Yield: 5.1 g (34.4 mmol, 99%), yellowish solid

Melting point: 76.5–82.2° C.

1H-NMR (400 MHz, D$_2$O): δ=3.98 (ddd, 1H, H-1eq), 3.89 (dd, 1H, H-6a), 3.70 (dd, 1H, H-6b), 3.66 (mc, 1H, H-3), 3.53 (ddd, 1H, H-1ax), 3.33–2.24 (m, 2H, H-4, H-5), 2.01 (mc, 1H, H-2eq), 1.64 (dddd, 1H, H-2ax) ppm; $J_{1eq,1ax}$=12.5, $J_{1ax,2ax}$=12.5, $J_{1ax,2eq}$=2.0, $J_{1eq,2ax}$=5.1, $J_{1eq,2eq}$=2.0, $J_{2eq,2ax}$=12.5, $J_{2ax,3}$=12.5, $J_{5,6a}$=2.0, $J_{5,6b}$=5.6, $J_{6a,6b}$=12.2 Hz.

EXAMPLE 3

(1S,3R,6R,10R)-3-(4'-(4"-Octyloxybenzoyloxy)phenyl)-10-hydroxy-2,4,7-trioxabicyclo[4.4.0]decane (3)

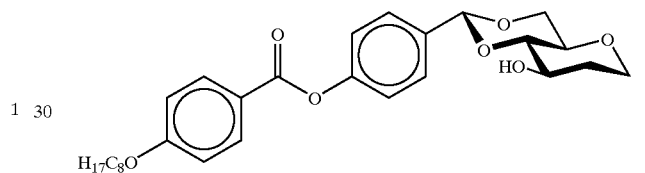

3

0.91 g (6.0 mmol) of 2 and 2.88 g (7.2 mmol) of 4-(octyloxybenzoyloxy)benzaldehyde dimethyl acetal were dissolved in 30 ml of anhydrous DMF, and a catalytic amount of 4-toluenesulfonic acid was added until the mixture was acidic. The reaction solution was agitated for about 5 hours in a rotary evaporator at 60–65° C. and a reduced pressure of 30 mbar. The reaction solution was neutralized using triethylamine, and the DMF was removed under reduced pressure. The crude product was recrystallized twice from 50 ml of methanol and washed with 30 ml of petroleum ether.

Yield: 2.61 g (5.4 mmol, 90%), colorless solid

Melting point: 138.8° C.

1H-NMR (400 MHz, C$_6$D$_6$): δ=8.21 (d, 2H, H-2Ar", H-6Ar"), 7.48 (d, 2H, H-2Ar', H-6Ar'), 7.14 (d, 2H, H-3Ar', H-5Ar'), 6.71(d, 2H, H-3Ar", H-5Ar"), 5.20 (s, 1H, H-3), 4.13 (dd, 1H, H-5eq), 3.55–3.43 (m, 5H, α-CH$_2$, H-5ax, H-10, H-8eq), 3.19 (dd, 1H, H-1), 3.06 (ddd, 1H, H-6), 2.98 (ddd, 1H, H-8ax), 2.25 (s, 1H, OH), 1.65–1.53 (m, 2H, H-9eq, H-9ax), 1.53–1.45 (m, 2H, β-CH$_2$), 1.31–1.10 (m, 10H, 5×CH$_2$), 0.87 (t, 3H, CH$_3$) ppm; $J_{Ar2",Ar3"}$=8.7, $J_{Ar5",Ar6"}$=8.7, $J_{Ar2',Ar3'}$=8.7, $J_{Ar5',Ar6'}$=8.7, $J_{5eq,6}$=4.6, $J_{5ax,5eq}$=10.2, $J_{1,6}$=10.2, $J_{1,10}$=10.2, $J_{5ax,6}$=10.2, $J_{8ax,8eq}$=11.2, $J_{8ax,9ax}$=11.2, $J_{8ax,9eq}$=4.0, $J_{Me,-CH2}$=7.1 Hz.

EXAMPLE 4

(1S,3R,6R,10R)-3-[4'-(4"-Octyloxybenzoyloxy)phenyl]-10-[4'''-(4''''-octyloxybenzoyloxy)benzoyloxy]-2,4,7-trioxabicyclo[4.4.0]decane (4)

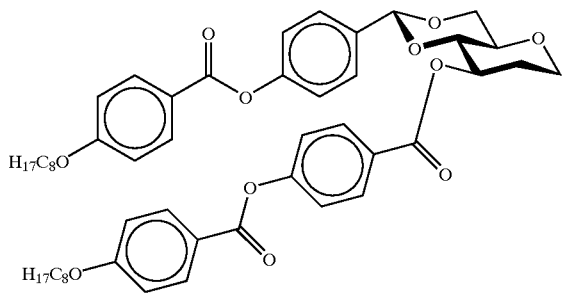

700 mg (1.45 mmol) of 3, 535 mg of 4-(4-octyloxybenzoyloxy)benzoic acid (1.45 mmol), 510 mg of DCC (2.47 mmol) and about 5 mg of 4-(1-pyrrolidinyl)pyridine were stirred at room temperature for about 20 hours in anhydrous dichloromethane.

For work-up, the reaction batch was evaporated to dryness under reduced pressure, the solid was taken up in diethyl ether, undissolved dicyclohexyl urea was filtered off, and the product was heated to the boil in about 125 ml of ethanol. After cooling, the resultant crystals were filtered off, washed with EtOH and dried under reduced pressure.

Yield: 994 mg (1.2 mmol, 82%), colorless solid

Melting point: 180.2° C.

1H-NMR (400 MHz, $C_6D_6$): δ=8.18–8.12 (m, 6H, H-2Ar", H-6Ar", H-2Ar''', H-6Ar''', H-2Ar"", H-6Ar""), 7.52 (d, 2H, H-2Ar', H-6Ar'), 7.04 (d, 4H, H-3Ar', H-5Ar', H-3Ar"", H-5Ar""), 6.73–6.66 (m, 4H, H-3Ar", H-5Ar", H-3Ar''', H-5Ar'''), 5.39 (ddd, 1H, H-10), 5.33 (s, 1H, H-3), 4.14 (dd, 1H, H-5eq), 3.62 (dd, 1H, H-1), 3.55–3.43 (m, 6H, 2×α-$CH_2$, H-5ax, H-8eq), 3.19 (ddd, 1H, H-6), 2.98 (ddd, 1H, H-8ax), 1.92 (mc, 1H, H-9eq), 1.92 (mc, 1H, H-9ax), 1.50 (sextet, 4H, 2×β-$CH_2$), 1.31–1.10 (m, 10H, 5×$CH_2$), 0.83 (t, 6H, 2×$CH_3$) ppm; $J_{Ar2',Ar3'}$=8.7, $J_{Ar5',Ar6'}$=8.7, $J_{Ar2''',Ar3'''}$=8.7, $J_{Ar5''',Ar6'''}$=8.7, $J_{1,10}$=10.2, $J_{9ax,10}$=10.2, $J_{9eq,10}$=5.1, $J_{5ax,5eq}$=10.2, $J_{5eq,6}$=5.1, $J_{1,6}$=9.7, $J_{8ax,8eq}$=11.2, $J_{8ax,9ax}$=11.2, $J_{\alpha\pm CH2,\beta\pm CH2}$=6.8, $J_{\beta\pm CH2,\gamma\pm CH2}$=6.8, $J_{-CH2,-Me}$=7.1 Hz.

EXAMPLE 5

(1S,3R,6R,10R)-3-(4'-methoxyphenyl)-10-hydroxy-2,4,7-trioxabicyclo[4.4.0]decane (5)

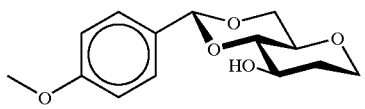

5.0 g (33.8 mmol) of 2 and 8.30 g (45.8 mmol) of p-methoxybenzaldehyde dimethyl acetal were dissolved in 50 ml of anhydrous DMA, and a catalytic amount of 4-toluenesulfonic acid was added until the mixture was acidic. The reaction solution was agitated for about 5 hours in a rotary evaporator at 60–65° C. and a reduced pressure of 30 mbar. The reaction solution was neutralized using triethylamine. 300 ml of ethyl acetate were added, and the mixture was extracted three times with water. The organic phase was dried over $Na_2SO_4$, the drying agent was filtered off, and the residue was evaporated under reduced pressure. The crude product was dissolved in a little ethyl acetate, precipitated using n-hexane, filtered off with suction and dried under reduced pressure.

Yield: 4.50 g (16.9 mmol, 50%), colorless solid

EXAMPLE 6

(1S,3R,6R,10R)-3-[4'-methoxyphenyl]-10-[4"-(acryloxybutyloxycarbonyloxy)benzoyloxy]-2,4,7-trioxabicyclo[4.4.0]decane (6)

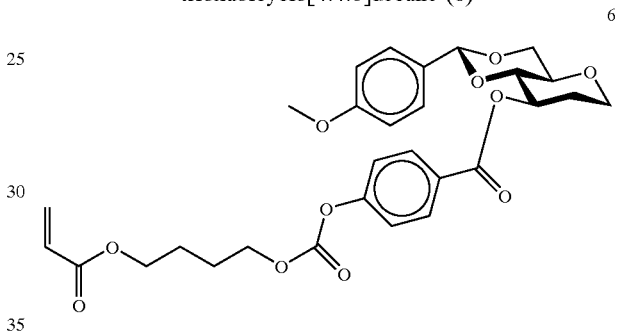

5.0 g (18.8 mmol) of 5, 5.79 g of 4-acryloxybutyloxycarbonyloxybenzoic acid (18.8 mmol), 6.60 g of DCC (32.0 mmol) and about 39 mg of 4-(1-pyrrolidinyl)pyridine were stirred at room temperature for about 24 hours in anhydrous dichloromethane.

For work-up, the reaction batch was evaporated to dryness under reduced pressure, the solid was taken up in diethyl ether, and insoluble dicyclohexyl urea was filtered off. The filtrate was evaporated and purified by column chromatography.

Yield: 8.15 g (14.7 mmol, 78%), colorless solid

EXAMPLE 7

Preparation of Cholesteric Pigments

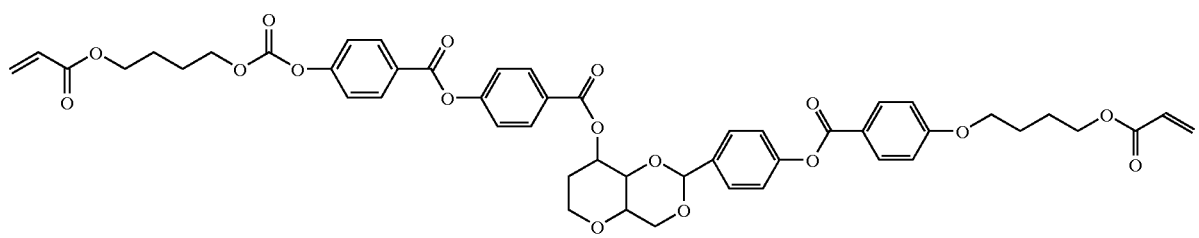

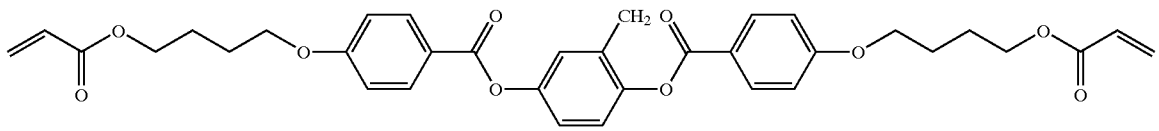

Use was made of a cholesteric liquid-crystalline mixture comprising, as chiral monomer, a compound of the formula 7 given above and, as achiral, nematic monomer, a compound of the formula 8 given above. The undiluted cholesteric mixture comprised 94.8% by weight of the achiral, nematic compound, 5.2% by weight of the chiral compound and, as photoinitiator, 2% by weight, based on the cholesteric liquid-crystalline mixture, of 1-hydrocyclohexyl phenyl ketone, which is marketed under the name Irgacure 184. The mixture exhibited a $\lambda_{max}$=350 nm (T=70° C.)

In order to prepare the pigments, this mixture was dissolved in methyl ethyl ketone and, for coating, applied to a polyethylene terephthalate film. The coating was carried out by the method described in DE-A 19 63 8797.

The thickness of the cholesteric layer was 2.5 μm. After the solvent had been evaporated at 70° C., the layer was crosslinked and cured by UV irradiation. The cured cholesteric material layer obtained in this way was detached from the substrate and graded by grinding and subsequent sieving. The particle size of the pigment particles was in the range <50 μm.

Preparations

EXAMPLE 8
Composition for Lip Care
Content by weight
(% by weight)

| | |
|---|---|
| to 100 | eucerinum anhydricum |
| 10.00 | glycerol |
| 5.00 | pigment (Example 7) |
| 8.00 | octyl methoxycinnamate |
| 5.00 | zinc oxide |
| 4.00 | castor oil |
| 4.00 | pentaerythrityl stearate/caprate/caprylate adipate |
| 3.00 | glyceryl stearate SE |
| 2.00 | beeswax |
| 0.50 | tocopheryl acetate |
| 2.00 | microcrystalline wax |
| 2.00 | quaternium-18 bentonite |
| 1.50 | PEG-45/dodecyl glycol copolymer |

EXAMPLE 9
Composition for Sun Blocker Containing Micropigments
Content by weight
(% by weight)

| | |
|---|---|
| to 100 | water |
| 10.00 | octyl methoxycinnamate |
| 6.00 | PEG-7-hydrogenated caster oil |
| 6.00 | titanium dioxide |
| 5.00 | pigment (Example 7) |
| 5.00 | mineral oil |
| 5.00 | isoamyl p-methoxycinnamate |
| 5.00 | propylene glycol |
| 3.00 | jojoba oil |
| 3.00 | 4-methylbenzylidene camphor |
| 2.00 | PEG-45/dodecyl glycol copolymer |
| 1.00 | dimethicon |
| 0.50 | PEG-40-hydrogenated caster oil |
| 0.50 | tocopheryl acetate |
| 0.50 | phenoxyethanol |
| 0.20 | EDTA |

EXAMPLE 10
Fat-free Gel
Content by weight
(% by weight)

| | |
|---|---|
| to 100 | water |
| 8.00 | octyl methoxycinnamate |
| 5.00 | pigment (Example 7) |
| 5.00 | glycerol |
| 5.00 | PEG-25 PABA |
| 1.00 | 4-methylbenzylidene camphor |
| 0.40 | acrylate C10–C30 alkyl acrylate crosspolymer |
| 0.30 | imidazolidinyl urea |
| 0.25 | hydroxyethyl cellulose |
| 0.25 | sodium methylparaben |
| 0.20 | disodium EDTA |
| 0.15 | fragrance |
| 0.15 | sodium propylparaben |
| 0.10 | sodium hydroxide |

EXAMPLE 11
Sun Cream (SPF 20)
Content by weight
(% by weight)

| | |
|---|---|
| to 100 | water |
| 8.00 | octyl methoxycinnamate |
| 6.00 | PEG-7-hydrogenated castor oil |
| 5.00 | pigment (Example 7) |
| 6.00 | mineral oil |
| 5.00 | zinc oxide |
| 5.00 | isopropyl palmitate |
| 5.00 | imidazolidinyl urea |
| 3.00 | jojoba oil |
| 2.00 | PEG-45/dodecyl glycol copolymer |
| 1.00 | 4-methylbenzylidene camphor |
| 0.60 | magnesium stearate |
| 0.50 | tocopheryl acetate |
| 0.25 | methylparaben |
| 0.20 | disodium EDTA |
| 0.15 | propylparaben |

EXAMPLE 12
Water-resistant Sun Cream
Content by weight
(% by weight)

| | |
|---|---|
| to 100 | water |
| 8.00 | octyl methoxycinnamate |
| 5.00 | PEG-7-hydrogenated castor oil |
| 5.00 | propylene glycol |
| 4.00 | isopropyl palmitate |
| 4.00 | caprylic/capric triglyceride |
| 5.00 | pigment (Example 7) |
| 4.00 | glycerol |
| 3.00 | jojoba oil |
| 2.00 | 4-methylbenzylidene camphor |
| 1.50 | PEG-45/dodecyl glycol copolymer |
| 1.50 | dimethicon |
| 0.70 | magnesium sulfate |
| 0.50 | magnesium stearate |
| 0.50 | tocopheryl acetate |
| 0.15 | fragrance |

EXAMPLE 13
Sun Milk (SPF 6)
Content by weight
(% by weight)

| | |
|---|---|
| to 100 | water |
| 10.00 | mineral oil |
| 6.00 | PEG-7-hydrogenated castor oil |
| 5.00 | isopropyl palmitate |
| 3.50 | octyl methoxycinnamate |
| 3.00 | pigment (Example 7) |
| 3.00 | caprylic/capric triglyceride |
| 3.00 | jojoba oil |
| 2.00 | PEG-45/dodecyl glycol copolymer |
| 0.70 | magnesium sulfate |
| 0.60 | magnesium stearate |
| 0.50 | tocopheryl acetate |
| 0.30 | glycerol |
| 0.25 | methylparaben |
| 0.15 | propylparaben |

We claim:

1. A method for producing a liquid crystalline composition which comprises doping a nematic or cholesteric base material for the generation of layers which reflect in color in the UV or IR region or for the preparation of pigments having a liquid-crystalline, cholesteric order with a compound of the formula I

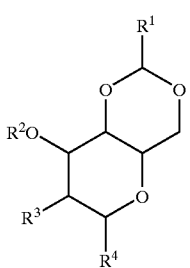

I in which the substituents have the following meanings:
$R^1$ is $Z^1$—$Y^1$—$(A^1)_m$—$Y^2$—$M^1$—$Y^3$—$(A^2)_n$—$Y^4$—;
$R^2$ is $Z^2$—$Y^5$—$(A^3)_o$—$Y^6$—$M^2$—$Y^7$—$(A^4)_p$—$Y^{11}$—;
$R^3$ and $R^4$ are hydrogen;
$A^1$ to $A^4$ are spacers having a chain length of from 1 to 6 carbon atoms;
$Y^1$ to $Y^7$ are chemical bonds, —O—, —S—, —C(=O)—, —C(=O)—O—, —O—C(=O)—;
$Y^{11}$ is a chemical bond, —C(=O)— or —O—C(=O)—;
$M^1$ and $M^2$ are mesogenic radicals selected from the group consisting of:

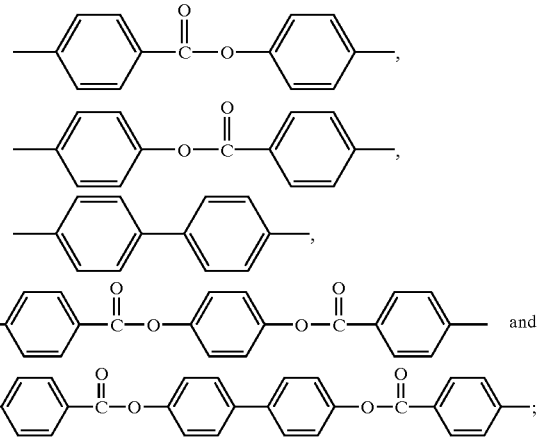

$Z^1$ and $Z^2$ are hydrogen, $C_4$–$C_{10}$-alkyl, polymerizable groups or radicals carrying polymerizable groups;
m is 0 or 1;
n is 0;
o is 0 or 1; and
p is 0,
where at least one of the radicals $Y^3$ and $Y^4$ or $Y^7$ and $Y^{11}$ is a chemical bond.

2. The process of claim 1 wherein at least one of the radicals $Z^1$ to $Z^2$ is a polymerizable group or a radical containing a polymerizable group.

3. The process of claim 1 in which said compound of formula I is a compound Ia

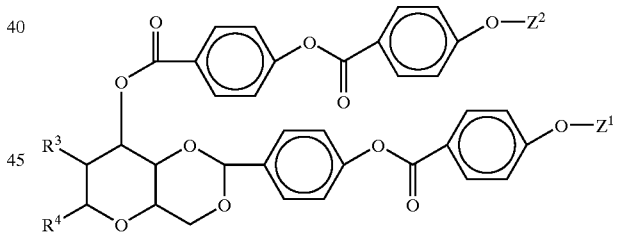

in which the substituents, independently of one another, have the following meanings:
$R^3$ is hydrogen;
$R^4$ is hydrogen;
$Z^1$ and $Z^2$ are hydrogen, $C_4$–$C_{10}$-alkyl, polymerizable groups or radicals carrying polymerizable groups.

4. A cholesteric liquid-crystalline composition comprising
a) at least one chiral liquid-crystalline monomer of the general formula I in which the substituents have the following meanings:
$R^1$ is $Z^1$—$Y^1$—$(A^1)_m$—$Y^2$—$M^1$—$Y^3$—$(A^2)_n$—$Y^4$—;
$R^2$ is $Z^2$—$Y^5$—$(A^3)_o$—$Y^6$—$M^2$—$Y^7$—$(A^4)_p$—$Y^{11}$—;
$R^3$ and $R^4$ are hydrogen;
$A^1$ to $A^4$ are spacers having a chain length of from 1 to 6 carbon atoms;
$Y^1$ to $Y^7$ are chemical bonds, —O—, —S—, —C(=O)—, —C(=O)—O—, —O—C(=O)—;

$Y^{11}$ is a chemical bond, —C(=O)— or —O—C(=O)—;
$M^1$ and $M^2$ are mesogenic radicals selected from the group consisting of:

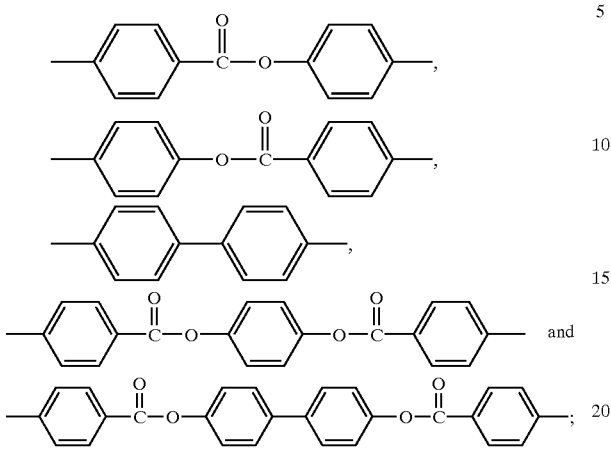

$Z^1$ and $Z^2$ are hydrogen, $C_4$–$C_{10}$-alkyl, polymerizable groups or radicals carrying polymerizable groups;
m is 0 or 1;
n is 0;
o is 0 or 1; and
p is 0,
where at least one of the radicals $Y^3$ and $Y^4$ or $Y^7$ and $Y^{11}$ is a chemical bond,

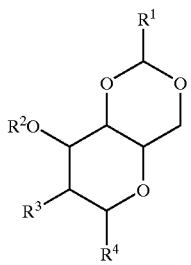

I or
b) a mixture of
$b_1$) at least one achiral, liquid-crystalline, polymerizable monomer of the general formula II

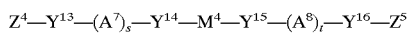

II in which the variables, independently of one another, have the following meanings:
$A^7$ and $A^8$ are spacers having a chain length of from 1 to 30 carbon atoms;
$M^4$ is a mesogenic group;
$Y^{13}$ to $Y^{16}$ are chemical bonds, —O—, —S—, —C(=O)—, —C(=O)—O—, —O—C(=O)—, —CH=CH—C(=O)—O—, —O—C(=O)—O—, —C(=O)—N($R^7$)— or —($R^7$)N—C(=O)—, —CH$_2$—O—, —O—CH$_2$—, —CH=N—, —N=CH— or —N=N—;
$R^7$ is hydrogen or $C_1$–$C_4$-alkyl;
s is 0 or 1;
t is 0 or 1;

$Z^4$ and $Z^5$ are hydrogen, $C_1$–$C_{12}$-alkyl, polymerizable groups or radicals carrying polymerizable groups, where the radicals $A^7$ and $A^8$ and $Y^{13}$ to $Y^{16}$ may be identical or different, at least one of the variables $Z^4$ or $Z^5$ is a polymerizable group or a radical carrying a polymerizable group, and, in the case where one or both of the indices s and t are zero, at least one of the radicals $Y^{13}$ and $Y^{14}$ or $Y^{15}$ and $Y^{16}$ is a chemical bond, and $b_2$) at least one chiral liquid-crystalline monomer of the general formula I.

5. A cholesteric liquid-crystalline composition as claimed in claim 4, comprising, as chiral liquid-crystalline monomer a) or $b_2$), at least one chiral compound of the general formula Ia,

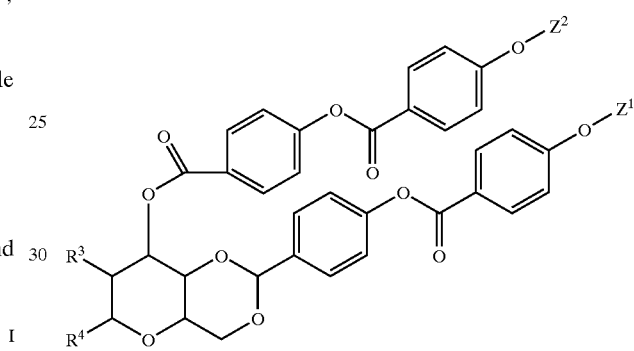

Ia in which the substituents, independently of one another, have the following meanings:
$R^3$ is hydrogen;
$R^4$ is hydrogen;
$Z^1$ and $Z^2$ are hydrogen, $C_4$–$C_{10}$-alkyl, polymerizable groups or radicals carrying polymerizable groups.

6. A cholesteric liquid-crystalline composition as claimed in claim 4, which reflects left-handed circular-polarized light in the UV region.

7. A pigment comprising a cholestric liquid crystalline composition as defined in claim 4.

8. A pigment as claimed in claim 7, which is a multilayer pigment.

9. A cosmetic or pharmaceutical preparation for protecting the human epidermis or human hair against UV light in the region from 280 to 400 nm, which comprises, alone or together with UV-absorbent compounds known per se for cosmetic and pharmaceutical preparations, an amount effective as a photostable UV filter of a cholesteric liquid-crystalline composition as defined in claim 8 in a cosmetically or pharmaceutically suitable excipient.

10. A cosmetic or pharmaceutical preparation as claimed in claim 9 comprising, as UV filter, a cholesteric liquid-crystalline composition in the form of a pigment.

11. A cosmetic or pharmaceutical preparation as claimed in claim 9 comprising, as UV filter, a cholesteric liquid-crystalline composition in the form of a multilayered pigment.

12. A chiral dopant of the general formula Ib $$\text{Ib}$$

(structure: bicyclic dioxane-pyran with R¹ at acetal carbon and R²O substituent)

in which the substituents, independently of one another, have the following meanings:

R¹ is $Z^1-Y^1-(A^1)_m-Y^2-M^1-Y^3-(A^2)_n-Y^4-$;

R² is hydrogen, $C_1-C_{12}$-alkyl, $C_1-C_{12}$-alkylcarbonyl, aryl, arylcarbonyl or $Z^2-Y^5-(A^3)_o-Y^6-M^2-Y^7-(A^4)_p-Y^{11}-$;

$A^1$ to $A^4$ are spacers having a chain length of from 1 to 30 carbon atoms;

$M^1$ and $M^2$ are mesogenic groups;

$Y^1$ to $Y^7$ are chemical bonds, $-O-$, $-S-$, $-C(=O)-$, $-C(=O)-O-$, $-O-C(=O)-$, $-CH=CH-C(=O)-O-$, $-O-C(=O)-O-$, $-C(=O)-N(R)-$ or $-(R)N-C(=O)-$, $-CH_2-O-$, $-O-CH_2-$, $-CH=N-$, $-N=CH-$ or $-N=N-$;

$Y^{11}$ is a chemical bond, $-C(=O)-$, $-O-C(=O)-$, $-CH=CH-C(=O)-$, $-(R)N-C(=O)-$, $-CH_2-$ or $-O-CH_2-$;

R is hydrogen or $C_1-C_4$-alkyl;

$Z^1$ and $Z^2$ are hydrogen, $C_1-C_{12}$-alkyl, polymerizable groups or radicals carrying polymerizable groups;

m to p are 0 or 1, where the radicals $A^1$ to $A^4$, $Y^1$ to $Y^7$ and $Z^1$ and $Z^2$ may be identical or different, and where, in the case where one or more of the indices m to p are zero, at least one of the radicals Y in each case adjacent to A is a chemical bond.

13. A chiral dopant as claimed in claim 12, in which the substituents have the following meanings:

R¹ is $Z^1-Y^1-(A^1)_m-Y^2-M^1-Y^3-(A^2)_n-Y^4-$;

R² is $Z^2-Y^5-(A^3)_o-Y^6-M^2-Y^7-(A^4)_p-Y^{11}-$;

$A^1$ and $A^3$ are spacers having a chain length of from 1 to 6 carbon atoms;

$Y^1$ to $Y^7$ are chemical bonds, $-O-$, $-S-$, $-C(=O)-$, $-C(=O)-O-$, $-O-C(=O)-$, $-CH=CH-C(=O)-O-$, $-O-C(=O)-O-$, $-C(=O)-N(R)-$ or $-(R)N-C(=O)-$, $-CH_2-O-$, $-O-CH_2-$, $-CH=N-$, $-N=CH-$ or $-N=N-$;

$Y^{11}$ is a chemical bond, $-C(=O)-$, $-O-C(=O)-$, $-CH=CH-C(=O)-$, $-(R)N-C(=O)-$, $-CH_2-$ or $-O-CH_2-$;

$M^1$ and $M^2$ are mesogenic radicals from the group consisting of:

(five mesogenic structures shown)

$Z^1$ and $Z^2$ are hydrogen, $C_4-C_{10}$-alkyl, polymerizable groups or radicals carrying polymerizable groups;

m is 0 or 1;

n is 0;

o is 0 or 1;

p is 0, where at least one of the radicals $Y^3$ and $Y^4$ or $Y^7$ and $Y^{11}$ is a chemical bond.

14. A chiral dopant as claimed in claim 12, of the general formula Ia, $$\text{Ia}$$

in which the substituents, independently of one another, have the following meanings:

$Z^1$ and $Z^2$ are hydrogen, $C_4-C_{10}$-alkyl, polymerizable groups or radicals carrying polymerizable groups.

* * * * *

UNITED STATES PATENT AND TRADEMARK OFFICE
CERTIFICATE OF CORRECTION

PATENT NO.   : 6,569,355 B1  Page 1 of 1
DATED        : May 27, 2003
INVENTOR(S)  : Prechtl et al.

It is certified that error appears in the above-identified patent and that said Letters Patent is hereby corrected as shown below:

<u>Column 43,</u>
Lines 33-44, the formula should be on Column 42, after "general formula I" on line 59.

Signed and Sealed this

Twenty-third Day of September, 2003

JAMES E. ROGAN
*Director of the United States Patent and Trademark Office*